US006670505B1

(12) United States Patent
Collins et al.

(10) Patent No.: US 6,670,505 B1
(45) Date of Patent: Dec. 30, 2003

(54) PROCESS FOR THE RECOVERY OF ORGANIC ACIDS FROM AQUEOUS SOLUTIONS

(75) Inventors: Nick Allen Collins, Fall Branch, TN (US); Mark Robert Shelton, Kingsport, TN (US); George William Tindall, Church Hill, TN (US); Steven Thomas Perri, Kingsport, TN (US); Ruairi Seosamh O'Meadhra, Kingsport, TN (US); Chester Wayne Sink, Kingsport, TN (US); Bhaskar Krishna Arumugam, Kingsport, TN (US); John Clark Hubbs, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/519,936

(22) Filed: Mar. 7, 2000

(51) Int. Cl.$^7$ .................. C07C 51/42; C07C 59/245; C07C 59/265; C07C 59/255; C12P 7/60

(52) U.S. Cl. .................. 562/580; 562/582; 562/584; 562/585; 562/589; 435/138; 435/803; 435/896; 435/876

(58) Field of Search .................. 560/176, 608; 562/577, 593, 513, 580, 582, 584, 585, 589; 435/138, 803, 876

(56) References Cited

U.S. PATENT DOCUMENTS

| | | | | |
|---|---|---|---|---|
| 2,318,500 A | * | 5/1943 | King et al. ......... | 549/315 |
| 2,421,611 A | * | 6/1947 | Gray ......... | 435/138 |
| 2,421,612 A | | 6/1947 | Gray ......... | 562/513 |
| 2,462,251 A | | 2/1949 | Bassford, Jr. et al. ...... | 562/513 |
| 2,918,492 A | * | 12/1959 | Hathaway ......... | 560/174 |
| 3,043,749 A | * | 7/1962 | Huang ......... | 435/138 |

(List continued on next page.)

FOREIGN PATENT DOCUMENTS

EP 0 483 831 A1 5/1992

OTHER PUBLICATIONS

John R. Holum, The Bronsted Definitions of Acids and Bases, WJ, Second ed., p. 177.*
Anderson, et al., "Production of 2–Keto–L–Gulonate, an Intermediate in L–Ascorbate Synthesis, by a Genetically Modified *Erwinia herbiocola*," Science, vol. 230, pp. 144–149 (1985).

(List continued on next page.)

Primary Examiner—Alan L. Rotman
Assistant Examiner—Taylor V. Oh
(74) Attorney, Agent, or Firm—Bernard J. Graves; Eric Middlemas

(57) ABSTRACT

A process for recovering a desired organic acid from a solution includes the steps of: providing an aqueous solution including at least one desired organic acid or its acid anion; adjusting the proton concentration in the aqueous solution to a desired level, with the desired proton concentration being selected, at least in part, by the amount of available protons needed to associate with the acid anions of the desired organic acid(s) to be recovered and/or acid anions that are weaker than the desired organic acids; and recovering at least a portion of the at least one desired organic acid from the aqueous phase. The desired proton concentration can be based on the amount of available protons being greater than, less than or substantially equal, to the amount of protons needed to associate with the anion of the desired organic acid(s) and acid anions that are weaker than the desired organic acid(s).

Specific examples of suitable organic acids include, but are not limited to, ascorbic, succinic, tartaric, glyconic, gulonic, citric, lactic, hialic, maleic, acetic, formic, gluconic pyruvic, propionic, butyric, itaconic acids and mixtures thereof. One embodiment of the present invention relates to the recovery of 2-keto-L-gulonic acid (KLG) from aqueous solutions such as fermentation baths.

12 Claims, 3 Drawing Sheets

Improper Protonation is Magnified During Acid Recovery

U.S. PATENT DOCUMENTS

| | | | |
|---|---|---|---|
| 3,234,105 A | * 2/1966 | Motizuki et al. | 435/138 |
| 3,381,027 A | * 4/1968 | Jaffe et al. | 560/174 |
| 4,113,771 A | 9/1978 | Lawrence, Jr. et al. | 562/568 |
| 4,191,841 A | 3/1980 | Soreau et al. | 562/475 |
| 4,202,828 A | 5/1980 | Matsuura et al. | 562/408 |
| 4,334,074 A | 6/1982 | Peterson | 546/327 |
| 4,699,999 A | 10/1987 | El-Chahawi et al. | 562/450 |
| 4,771,001 A | 9/1988 | Bailey et al. | 435/139 |
| 4,990,441 A | 2/1991 | Barthole et al. | 435/138 |
| 5,128,487 A | 7/1992 | Tomislav et al. | 569/315 |
| 5,159,110 A | 10/1992 | Thunberg | 562/554 |
| 5,168,055 A | 12/1992 | Datta et al. | 435/145 |
| 5,202,475 A | 4/1993 | Cook et al. | 562/513 |
| 5,202,476 A | * 4/1993 | Tsuda et al. | 562/513 |
| 5,210,296 A | 5/1993 | Cockrem et al. | 562/589 |
| 5,349,074 A | 9/1994 | Bonaldi | 552/851 |
| 5,391,770 A | 2/1995 | Le Fur et al. | 549/315 |
| 5,410,076 A | 4/1995 | Coope et al. | 562/450 |
| 5,426,219 A | 6/1995 | Lehnhardt et al. | 562/580 |
| 5,449,824 A | 9/1995 | Felman et al. | 562/580 |
| 5,522,995 A | 6/1996 | Cockrem | 210/637 |
| 5,712,131 A | 1/1998 | Felman et al. | 435/136 |
| 5,741,681 A | 4/1998 | Kato et al. | 635/109 |
| 5,827,700 A | 10/1998 | Felman et al. | 435/144 |
| 5,852,211 A | 12/1998 | Dümpelmann et al. | 562/580 |

OTHER PUBLICATIONS

Reichstein, ed al., "Eine Ergiebige Synthese der l–Ascorbinsäure (C–Viamin)$^2$)," Helv. Chim. Acta, vol. 17:311–328 (1934).

Saito, et al., "Cloning of Genes Coding for L–Sorbose and L–Sorbosone Dehydrogenases from *Gluconobacter oxydans* and Microbial Production of 2–Keto–L–Gulonate, a Precursor of L–Ascorbic Acid, in a Recombinant *G. oxydans* Strain," Applied & Environmental Microbiol., 63(2):454–460 (1997).

* cited by examiner

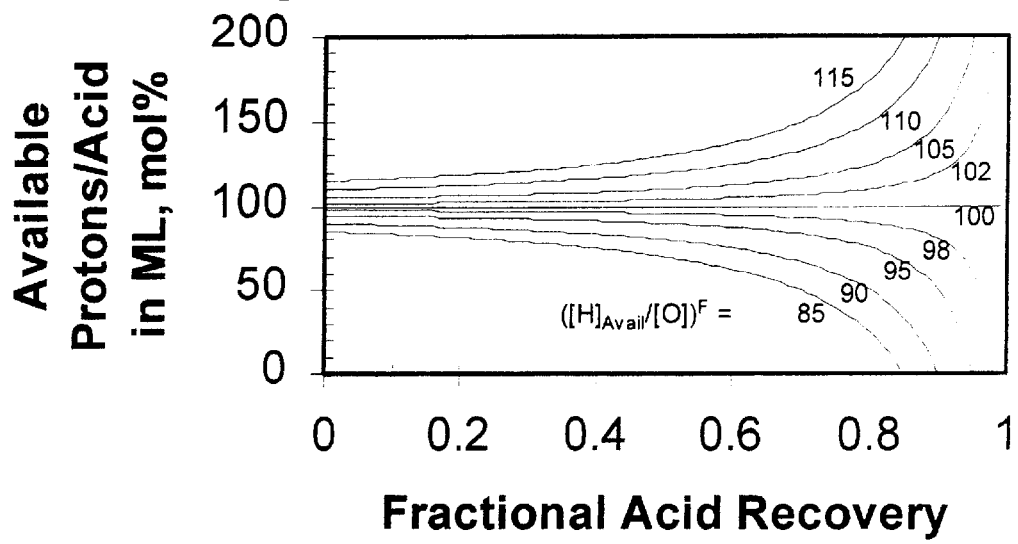
Figure 1 - Improper Protonation is Magnified During Acid Recovery

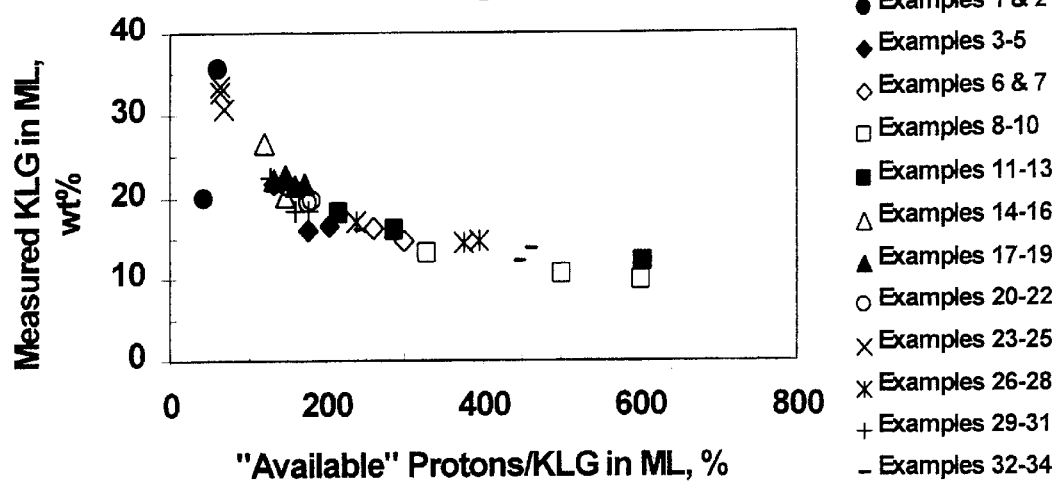
Figure 2 - Solubility Decreases with Increasing Protonation

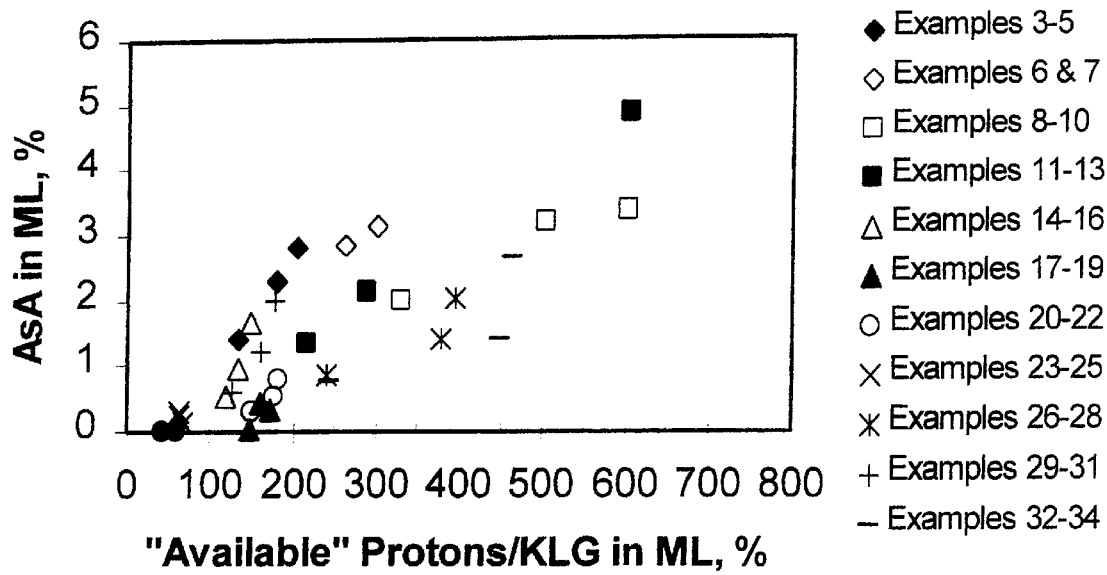

PROCESS FOR THE RECOVERY OF ORGANIC ACIDS FROM AQUEOUS SOLUTIONS

BACKGROUND OF THE INVENTION

1. Field of the Invention

The present invention relates to an improved method for recovering of organic acids, and in particular degradation-sensitive organic acids, from a solution.

2. Background of the Invention

It is often necessary to recover organic acids from solution. To this end, solutions containing organic acids can originate from a variety of chemical reactions and biological processes such as fermentation processes.

A typical approach to dealing with acid recovery involves the protonation of the carboxylate or salt form of the acid to reach a desired pH level.

For example, a process for the manufacture of syringic acid is taught in U.S. Pat. No. 4,191,841 in which an aqueous solution containing the double alkali salt of the acid is acidified with a strong acid such as hydrochloric or sulfuric acid followed by crystallizing the carboxylic acid product. The amount of strong acid addition is that sufficient to bring the solution pH to 3.

U.S. Pat. No. 4,202,828 describes a process to recover naphthoquinone and phthalic acid from a gas stream with an aqueous solvent formed by recycling the neutralized filtrate from naphthoquinone extraction and phthalic acid crystallization. The filtrate is treated with a base to a pH of 1.2 to 2.5, preferably 1.5 to 2.2, to neutralize only sulfuric acid and maleic acid byproducts without neutralizing unrecovered phthalic acid.

Acidification with hydrochloric acid to recover 3,6-dichloropicolinic acid from an aqueous solution of its salts in the process taught in U.S. Pat. No. 4,334,074. Once again, pH is used to determine the level of acidification.

Recovery of carboxylic acids, especially N-acetyl-DL-phenylalanine carboxylic acid, made via carbonylation using cobalt carbonyl catalyst is taught in U.S. Pat. No. 4,699,999. After removal of cobalt salt and any organic phase, the carboxylic acid is recovered from the aqueous phase by precipitating it with acids, especially mineral acids such as hydrochloric, sulfuric, or phosphoric acid, with the amount of acid addition based on a target pH of 1.

The recovery of N-methyliminodiacetic acid from an aqueous solution containing its disodium salt is described in U.S. Pat. No. 5,159,110. In this process, the solution is acidified using sulfuric acid and concentrated to precipitate sodium sulfate. Acidification is controlled by solution pH, with a target of approximately 2, the isoelectric point of the carboxylic acid.

Crystallization recovery of a dicarboxylic acid from an aqueous solution containing its disodium salt is also taught in U.S. Pat. No. 5,202,475. In this case the organic acid is 1,3- or 1,4-cyclohexanedicarboxylic acid, protonation is with hydrochloric or sulfuric acid, and the precise control of the acidification process via solution pH is again emphasized with preferred targets of 2.8 and 2.6 for the 1,4- and 1,3-isomers, respectively.

The recovery of hyodeoxycholic acid from swine bile is taught in U.S. Pat. No. 5,349,074. After isolation of the acid from other biliary acids and bile components as its magnesium salt, the solid hyodeoxycholic acid magnesium salt is suspended in an ethyl acetate aqueous solution and acidified with a mineral acid to produce the acid form. Solution pH is used to control acidification with a desired pH of 1 to 3.

The preparation of bis(amidocarboxylic acids), especially N,N'-terephthaloyl-di(6-aminocaproic acid), under basic conditions is described in U.S. Pat. No. 5,410,076 in which the product is recovered by selective precipitation. Sulfuric acid was used to lower the pH and precipitate the organic acid with a pH of between about 5.5 and 6.5 disclosed as providing a highest purity.

An enzymatic method for producing L-aspartic acid from maleic acid is taught in U.S. Pat. No. 5,741,681 in which the reactions occur with the acids in their ammonium salt forms. Acidification to an isoelectric point of L-aspartic acid of 2.8 is disclosed as providing an improved recovery.

This reliance on pH for preformation is also prevalent in the context of organic acid recovery from fermentation broths.

For example, the production of lactic acid by fermentation followed by recovery utilizing extraction is described in U.S. Pat. No. 4,771,001. Prior to extraction the fermentation broth is acidified to a desired pH level.

The recovery of lactate esters and lactic acid from fermentation broth is described in U.S. Pat. No. 5,210,296 where the lactate salts are acidified in the presence of an alcohol of 4-5 carbon atoms. A strong acid such as sulfuric acid is added until the pH is between 1.0 and 1.6.

A process for recovering organic acids, especially lactic acid, from aqueous solutions such as fermentation broth is taught in U.S. Pat. No. 5,426,219 in which the solution is acidulated prior to extraction. Mineral acid is used to bring the pH between 1 and 4.5 before and during extraction.

Despite its widespread use, pH-based techniques have not proven to be consistently effective or even predictable.

For example, in those cases where the acid form of the organic compound is less soluble than the salt form, the desired carboxylic acid may be selectively precipitated by the addition of a stronger acid having a larger acid dissociation constant or smaller ($pK_a$) than the desired product. In certain cases, increasing this acidification reduces the solubility of the organic acid and can improve recovery.

However, in other cases, the desired acid decomposes in the presence of a strong acid. In such cases, recovery may actually decrease upon acidification despite the reduced solubility of the acid. The presence of organic or inorganic impurities only serves to further complicate the recovery process. For example, such impurities may dissociate into cationic and anionic components, they can either compete for protons with the carboxylic acid or may donate protons into the process. Neither result is desirable.

That is, the competition for protons effectively reduces recovery of the desired organic acid while donating protons into the process can cause decomposition of the desired acid. Moreover, while the level of such impurities is typically small relative to the desired organic acid, such impurities can become concentrated during the process, thus, further magnifying their effect.

In light of the foregoing, it is clear that the existing protonation techniques are ineffective to consistently remove desired organic acids from aqueous solutions.

A second problem relates to the presence of anions other than that associated with the acid to be recovered. It is recognized that in the recovery of organic acids from an aqueous solution, the concentration of other anions present in the solution can strongly influence the effectiveness of the recovery process. Because of this, the art has looked towards removing the undesirable anions-as well as adjusting the solution pH-in attempting to improve the recovery process. The ion exchange technique has been employed but is equally ineffective.

In this regard, the carboxylate or salt form of the desired acid may be converted to the acid form by treating the aqueous solution with a hydrogen or free-acid form of a cation exchange resin. While this ion exchange technique may remove most, if not all, of the inorganic cations from the aqueous solution, it will also introduce its own set of problems.

For example, the resin will also protonate other anions in the solution. As was the case above, this can lead to detrimental effects. In particular, the resultant impurity acids, whether organic or inorganic in nature, are often stronger than the desired organic acid and thus may lead to decomposition of the desired acid. The ion exchange process may further dilute the solution leading to a still further decrease in recovery.

Accordingly, the need still exist for a process for which effectively recovers a desired organic acid, and in particular, a degradation-sensitive organic acid.

One organic acid of particular interest to the inventors is 2-keto-L-gulonic acid (KLG). To this end, techniques for the recovery of 2-keto-L-gulonic acid are also recognized in the art. However, existing techniques for the recovery of KLG are faced with a variety of problems in addition to the pH and ion-exchange problems discussed above.

For example, many of these techniques, such as those described in U.S. Pat. Nos. 2,421,611 and 2,421,612, teach crystallization recovery of this acid in its alkali or alkaline earth salt form followed by conversion to the acid form by treatment with an acid such as sulfuric. Such processes introduce a variety of problems insofar as yet another crystallization step is required to separate the 2-keto-L-gulonic acid from the aqueous acidification media for subsequent conversion steps such as esterification.

In addition, it is an art recognized belief that, in the production of a solid 2-keto-L-gulonic acid product, it is necessary to treat the aqueous solution with an anion exchange resin prior to recovery of the carboxylic acid using crystallization or extraction. See, for example, U.S. Pat. Nos. 4,990,441 and 5,202,476.

Thus, the need is particularly great for an improved process for the recovery of KLG from aqueous solutions such as fermentation broths.

SUMMARY OF THE INVENTION

The present invention is based, at least in part, on the surprising discovery that the optimum solution composition to recover desired organic acids cannot be effectively determined by pH measurements with or without the knowledge of the concentration of the organic acid in the solution.

Instead, the inventive process involves adjusting the proton level in the aqueous phase to a desired proton concentration where the proton concentration is selected, at least in part, relative to the amount of protons needed to associate with the organic acid to be recovered and the acid anions that are weaker than the organic acids to be recovered.

The present invention is based, at least in part, on the further surprising discovery that optimizing recovery of the desired acid does not require the removal of other anions from the solution. Accordingly, the inventive method can be effectively employed for separating a variety of acids from aqueous environments.

One aspect of the invention relates to a process for recovering a desired organic acid from a solution comprising the steps of:

(a) providing an aqueous solution including at least one desired organic acid or its acid anion;

(b) adjusting the proton concentration in the aqueous solution to a desired level, with the desired proton concentration being selected, at least in part, by the amount of available protons needed to associate with the acid anions of the desired organic acid(s) and/or acid anions that are weaker than the desired organic acids; and (c) recovering at least a portion of the at least one desired organic acid from the aqueous phase.

In this regard, the desired proton concentration can be based on the amount of available protons being greater than, less than or substantially equal, to the amount of protons needed to associate with the anion of the desired organic acid(s) and acid anions that are weaker than the desired organic acid(s).

Specific examples of suitable organic acids include ascorbic, succinic, tartaric, glyconic; gulonic, citric, lactic, malic, maleic, acetic, formic, pyruvic, propionic, gluconic, butyric, itaconic acids and mixtures thereof.

One embodiment of the present invention relates to the recovery of 2-keto-L-gulonic acid (KLG) from aqueous solutions such as fermentation baths.

BRIEF DESCRIPTION OF THE DRAWINGS

FIG. 1 illustrates the problems associated with improper protonation of the solution during the recovery process;

FIG. 2 illustrates that decrease in solubility associated with increasing protonation; and FIG. 3 illustrates the increase in ascorbic acid in mother liquor with increasing protonation.

DETAILED DESCRIPTION OF THE PREFERRED EMBODIMENTS

As discussed above, the present invention relates to a method for recovering organic acids and in particular, degradation-sensitive organic acids from a solution, preferably an aqueous solution.

By "degradation-sensitive" that is referring to those organic acids that are subject to decomposition in the presence of a strong acid.

In addition, preferred organic acids include those acids where the salt form of the acid is more soluble in the solvent than the acid itself While any organic acid can be employed in the present invention, carboxylic acids are preferred. Specific examples of suitable organic acids that can be recovered by the inventive method include succinic, tartaric, gluconic, glyconic, citric, lactic, malic, maleic, acetic, formic, pyruvic, propionic, butyric, itaconic, ascorbic, and gulonic acids.

As discussed above, the acid can be present in the acid or anionic form thereof. It is preferred that at least a portion of the acid be present in its anionic form. Examples of suitable water ions include alkali and alkaline earth salts with specific examples of suitable counter ions including sodium, potassium and calcium. The acid can also be present in an ammonium form.

The solution can include a variety of other components including other acids, acid anions, and/or neutral organics. Specific examples of suitable acid anions include phosphates, sulfates, nitrates and chlorides among others while suitable neutral organics include sugars, aldehydes and ketones.

Moreover, other components can be present depending on the nature and use of the particular aqueous solution. For example, in employing the present invention with aqueous solutions produced from fermentation, and in particular, the recovery of 2-keto-L-gulonic acid from fermentation broths, pH can be kept neutral or near neutral by the addition of a suitable base such as aqueous ammonia, calcium carbonate, calcium hydroxide, sodium hydroxide, sodium bicarbonate, sodium carbonate or the like to convert the organic acid product to carboxylate or salt form. In addition, unreacted sugars and other feed materials can be present.

As discussed above, the present invention can be performed without removal of other anions from the solution.

A first aspect of the inventive method involves a step where the proton concentration is adjusted. In this step, the aqueous solution is protonated to provide a desired proton concentration, with the desired proton concentration being based, at least in part, on the amount of protons needed to associate with the desired organic acid(s), e.g. those organic acids to be recovered, and acid anions that are weaker than the desired organic acid(s). Accordingly, this step of the process preferably involves (i) determining the state of protonation of the desired organic acid(s) and then (ii) adjusting the proton concentration to a desired level. Each of these preferred aspects of this adjustment will be discussed in detail below.

The state of protonation of the organic acid is referenced to the equivalence point. In the context of the invention, an acid is considered to be at equivalence if the solution contains enough protons to associate with the desired organic acid and all acid anions, organic or inorganic, that are weaker than the organic acid of interest, but not enough to associate with acid anions, organic or inorganic, that are stronger than this acid.

It is important to recognize that this definition is not meant to imply that the desired organic acid and weaker acid anions are fully associated in solution and the stronger acid anions are fully dissociated, but that there are enough protons available to associate with the desired organic acid anion and weaker acid anions with none left over for the stronger acid anion impurities.

It is further recognized that the degree of proton association with the various acid anions in a given solution will be dictated by principles of chemical equilibrium. And, even at equivalence there will be some dissociation of the desired organic acid and proton association with stronger acid anions.

The technique for determining the state of protonation is not critical to the invention. To this end, the preferred techniques include charge balance, titration, and spectroscopic methods.

As to ionic charge balance, the state of protonation of the organic acid may be determined using compositional analysis of the aqueous solution. The concentration of all species capable of forming cations or anions by dissociation should be known as well as the dissociation constants of the ionizable species present. This includes inorganic species such as alkali and alkaline earth metals generally present as cations in the solution and sulfur, phosphorus, chlorine, and the like indicative of strong acid anions. And, the concentration of the desired organic acid should be known as well as any other organic acid impurities present in significant quantities. It is especially important to know the concentration of any species capable of forming an acid stronger than the organic acid of interest as it is desirable to counter the negative charge of these anions with an inorganic cation rather than a proton.

By charge balance, the total concentration of protons in the aqueous solution is given by the following expression:

$$[H]_{Total} = \Sigma(v_i[A_i]) - \Sigma(v_j[C_j])$$

where $[A_i]$ is the molar concentration of anionic species i with a negative charge of $-v_i$ in its fully dissociated state and $[C_j]$ is the molar concentration of inorganic (i.e., excluding protons) cationic species j with a positive charge of $+v_j$. Again, this is not meant to imply that all of these protons are dissociated in solution. The total proton concentration $[H]_{Total}$ simply represents the sum of associated and dissociated protons before assigning them to any particular species.

For example, in a solution containing the inorganic species Ca, K, Na, Mg, S, P, and Cl and the organic acid O, the total proton concentration is given by $$[H]_{Total} = [O] + 2[S] + 3[P] + [Cl] - (2[Ca] + [K] + [Na] + 2[Mg])$$

This assumes that the organic acid contains a single carboxyl group, sulfur is present as the sulfate anion ($SO_4^{2-}$), phosphorus is present as phosphate anion ($PO_4^{3-}$), and all chlorine is inorganic chloride. Those skilled in the art can easily apply this relationship appropriately for other cases involving, for instance, multiple carboxyl groups on the organic acid or additional organic acids or inorganic electrolytes.

The state of protonation of the organic acid is found by determining the concentration of protons available to associate with the organic acid after assigning some of this total to any acid anions present that are weaker (higher $pK_a$) than the organic acid of interest. This concentration of available protons, $[H]_{Avail}$, is given by $$[H]_{Avail} = [H]_{Total} - \Sigma(\eta_k[W_k])$$

where $[W_k]$ is the concentration of weak acid anion k that remains weaker than the organic acid anion after associating with $\eta_k$ protons. Given the molar ratio of available protons to the organic acid equals one at equivalence (for a monocarboxylic acid), this ratio may be used as a quantitative measure of the degree of protonation.

For instance, in the above example if the $pK_a$ of the organic acid O is 2.5, the phosphate anion will associate with two protons to form the dihydrogen phosphate anion $H_2PO_4^-$ at conditions necessary to protonate the organic acid O so $$[H]_{Avail} = [H]_{Total} - 2[P]$$

for this example.

The $pK_a$'s of hydrochloric, the third proton of phosphoric, and both protons of sulfuric acid are lower than that of the organic acid in this case, so leaving the solution with only enough protons available for the organic acid helps prevent formation of these stronger acids. Again, even when the solution is at equivalence, there will be some dissociation of the desired organic acid and proton association with stronger acid anions. However, as the organic acid is removed from solution by extraction or crystallization, these stronger acids will donate any protons associated with their anions to the weaker organic acid.

Another method to determine the state of protonation involves the use of titration. Given the solution is at equivalence when the molar concentrations of available protons and organic acid are equal, the molar amount of protons to add (subtract) to reach equivalence, $H_{Eq}$, is given by $$H_{Eq} = O - H_{Avail}$$

where O is the molar amount of organic acid O present and $H_{Avail}$ is the molar amount of available protons in solution. Typically, $H_{Eq}$ would be determined by titration with a strong acid titrant in water solvent. However, for a relatively strong organic acid like 2-keto-L-gulonic acid (KLG), $H_{Eq}$ cannot be determined by titration with a strong acid in water because the organic acid anion is too weak a base to give an adequate end point.

Any solvent that is aprotic or at least a very weak acid can be employed in the titration of such organic acids. Moreover, the choice of preferred solvent is dependent on the acid in question. Specifically, dimethyl sulfoxide (DMSO) is preferred for obtaining a good end point with KLG solutions because it is aprotic and a good solvent for the titration components.

The presence of other acid or base species can complicate the titration of acid solutions. For example, in connection with KLG titration done in DMSO sulfate acts as a weak base along with the KLG anion that leads to an error in the amount of acid needed to reach equivalence. The addition of excess barium chloride before the titration eliminates problems caused by sulfate:

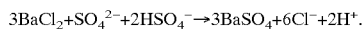

$$3BaCl_2 + SO_4^{2-} + 2HSO_4^- \rightarrow 3BaSO_4 + 6Cl^- + 2H^+.$$

Sulfate, and interference in the titration, is removed and the proton associated with bisulfate is freed to protonate the organic acid. Therefore, only dissociated organic acid anion and other weak acid anions are titrated and the amount of acid to reach equivalence in the titration reflects the amount needed to reach equivalence in the solution.

While the addition of barium chloride provides a convenient correction for the sulfate problem in DMSO, the titration could be done without it and a correction made based on the amount of sulfate as determined by ion chromatography or another technique. Similar considerations could be made for other components present at significant concentrations. Also, for the case in which available protons exceed those needed to protonate the organic acid, the titration could be performed with a strong base, or, alternatively, a known amount of strong base added and back titrated with acid.

A second aspect of the protonation step involves adjusting the proton concentration based, at least in part, on the state of protonation of the desired organic acid(s). This adjustment technique can involve one or more steps depending upon the particular organic acid to be recovered.

For example, when employing an aqueous solution containing the salt form of the desired organic acid(s), the adjustment can be performed in a single step by adding a proper amount of a strong acid. By strong acid, it is meant an acid that is strong in comparison to the organic acid being recovered. Suitable examples of strong acids for use with the preferred organic acids include hydrochloric, sulfuric, nitric and phosphoric acids.

Alternatively, a two-step process can be employed. In this embodiment, all of the acid ions, both weak and strong, can be protonated with an hydrogen or acid form of a cationic exchange resin followed by an addition of an appropriate amount of base for neutralization of the strong acids only.

Specific examples of suitable cation exchange resins include sulfonated polystyrene resins such as Ambersep 200H, Amberlite IR-118 H form, Dowex 50X2-100, 50X2-200, 50X2-400, 50X8-200, 50X8-400, HBK-530 H form, and HBK-550 form.

Depending on a particular base employed in neutralization, the two-step process may have the advantage of eliminating inorganic salt impurities in the organic acid product by first removing all of the inorganic cations such as calcium that can form insoluble or sparingly soluble salts. Moreover, it can be superior to the use of a cation exchange resin alone in that the strong acids produced by the cation exchange are neutralized so as to avoid decomposition problems.

In an alternative embodiment relating to the two-step process, a slip stream comprising the carboxylate-containing solution can be bypassed around the cation exchange step and used to neutralize the strong acids formed therein.

Yet another embodiment involves a three-step protonation technique. A suitable three-step technique could include:

(1) conversion of the bulk of the carboxylate to its acid form by treatment with a strong acid followed by removal of any precipitated salts;

(2) protonating any remaining acid ions with the hydrogen or acid form of a cation exchange resin, and finally, (3) adding an appropriate amount of base to neutralize resulting strong acids.

Specific examples of suitable bases include sodium hydroxide and potassium hydroxide.

This technique can be effectively employed in processes such as those processes where it is important to reduce the load on the cation exchange resin in those cases where the cation forming the salt produces an insoluble or sparingly soluble inorganic salt upon acidification with a mineral acid, such as sulfuric acid or hydrochloric acid.

In each of the techniques, the proton concentration can be adjusted to any desired level based upon the state of protonation of the desired organic acid. To this end, it is within the scope of the present invention to both overprotonate, i.e., provide a proton concentration greater than the equivalence level, as well as underprotonate, depending upon the particular acid to be recovered and the aqueous solution employed.

In particular, discussed above, over protonation may lead to the decomposition of the organic acid during subsequent evaporation or concentration steps, while under protonation will leave some of the organic acid in its carboxylic form which can potentially lead to salt impurities in the organic acid product or even lower yields of the acid product. However, the ability to determine and employ the state of protonation and determining proton concentration is a key aspect of the present invention. To this end, in most cases it is preferred that the proton concentration be adjusted such that the organic acid is at its equivalence.

The desired proton concentration is dependent on a number of factors including the precise organic acids to be removed, other anions in the system and the like.

Since solubility is generally minimized at high ratios of available protons to organic acid, it is often preferred that the aqueous solution be overprotonated relative to equivalence to maximize recovery. Where overprotonation is desired, the proton concentration is preferably about 1 to about 10% by mole greater than equivalence.

However, in certain circumstances overprotonation conditions may lead to decomposition of the organic acid during subsequent recovery, e.g, evaporation or concentration steps. In such cases, underprotonation can be preferred. In the case of underprotonation, preferred proton concentrations are on the order of about 1 to about 10% by mole less than equivalence.

On the other hand, underprotonating the solution will leave some of the organic acid in its carboxylate form potentially leading to salt impurities in the organic acid product or lower yields. Optimizing recovery via crystallization requires protonating the feed such that solubility is minimized without leading to unacceptable decomposition losses.

Accordingly, in many cases, adjusting the proton concentration so that the organic acid is at equivalence will be optimal.

This can be demonstrated by relating the state of protonation of the feed to that of the solution remaining after significant organic acid recovery. By material balance, one can derive the following relationship between the ratio of available protons to organic acid O in the feed ($[H]_{Avail}/[O])^F$ to that in the filtrate or mother liquor ($[H]Avail/[O])^{ML}$ after fractional recovery r of the acid:

$$([H]_{Avail}/[O])^{ML} = 100\% \left[1 - \frac{1}{(1-r)}\left(1 - \frac{([H]_{Avail}/[O])^F}{100\%}\right)\right]$$

This equation is plotted in FIG. 1 as a function of fractional recovery for feed $[H]_{Avail}/[O]$ values from 85 to 115%. At organic acid recoveries above 85%, the protonation level in the mother liquor deviates significantly from that of the feed for initial protonations other than equivalence (i.e., 100%). These deviations will dramatically impact solubility, decomposition, and, thus, the recovery actually attainable. So, unless it is desirable to operate subsequent recovery steps at $[H]_{Avail}/[O]$ ratios away from 100% due to solubility or decomposition concerns, the feed should be protonated to equivalence.

A preferred application for the inventive process relates to the formation of ascorbic acid and in particular, the recovery of 2-keto-L-gulonic acid.

To this end, the 2-keto-L-gulonic acid can be produced by any technique recognized within the art including fermentation, the Reichstein process and hydrolysis of diactone 2-keto-L-gulonic acid (2,3; 4,6-diisopropylidene-oxo-L-gulonic acid) monohydrate or its anhydride.

Alternatively, the inventive method can be employed with a recovery of variety of organic acids from aqueous solutions, and in particular, those aqueous solutions containing carboxylic genesis discussed within the background of the invention.

Subsequent to adjusting the proton concentration, the desired organic acid(s) are removed from the aqueous phase. To this end, the exact method for recovery is not critical to the claimed invention in that any recovery technique recognized within the art can be employed within the present invention.

For example, suitable techniques involve isolation of the desired organic acid(s) by crystallizing the acid from the aqueous phase followed by at least one of filtration, centrifugation, decantation, extraction and/or spray drying.

The inventive method can also include recycling or reuse of various streams produced therein. For example, such a recycle can include the aqueous phase remaining subsequent to recovery which is recycled by into the starting material in order to provide for additional removal of any remaining organic acid(s).

Moreover, the recycle stream(s) can be contacted with suitable anion or cation exchange resins prior to reintroduction into the aqueous solution.

The desired organic acid(s) can be employed in any art-recognized process. For example, where KLG is to be removed from an aqueous fermentation broth, the KLG can be used in the formation of ascorbic acid. Other uses for the various organic acids are well recognized in the art and as such need not be described in detail here.

The present invention is capable of providing a proper proton concentration in an aqueous stream containing a desired carboxylate or salt form of organic acid without the need of contacting the aqueous solution with an anion exchange resin. Moreover, this process allows for recovery of the desired acid product to be maximized during subsequent recovery steps. Finally, the present invention is capable of providing this recovery in a cost-effective manner.

The present invention will now be described in terms of certain specific examples. However, it should be recognized that these examples are only illustrative in nature and in no way limit the scope of the present invention.

EXAMPLES

The following examples relate to the recovery of 2-keto-L-gulonic acid (KLG) from fermentation broth via crystallization. Examples 1–44 are representative of prior art methods to protonate the KLG prior to crystallization while Examples 45–70 reflect proper protonation of the organic acid herein. In all cases the KLG-containing broths were prepared by aerobic fermentation of glucose and fructose feeds with a recombinant DNA organism and pH controlled to 5–6 with $Ca(OH)_2$ addition. As described in the following examples, the broths were typically acidified to pH~2 with sulfuric acid and clarified using activated carbon and filtration to remove cells, gypsum, and other inorganic salts before any additional treatments.

Example 1

After acidification to pH~2 with sulfuric acid, carbon treatment, and microfiltration to remove cells, carbon and other solids, 3031 grams of a broth with composition given in Table 1 was subjected to evaporative crystallization at 10° C. The broth was evaporated to the point at which the average concentration of soluble inorganics (K, Na, and P) increased by a factor of 7.52 in the mother liquor, or filtrate, relative to that in the feed and 2312.6 grams of distillate was recovered. After vacuum filtration, a methanol wash, and drying, 361.1 grams of a 86.6 wt % pure (anhydrous basis) KLG product was recovered corresponding to 77.9% KLG recovery. The composition of the mother liquor is given in Table 2. Comparison of the ratio of available protons to KLG as determined by charge balance in the feed (87.5%) to that in the mother liquor (60.9%) reveals that the feed broth was underprotonated and became even more proton deficient as KLG was crystallized. This was also reflected by the pH increase from 1.8 in the feed to 2.08 in the mother liquor.

Example 2

To simulate mother liquor recycle in a continuous crystallization process, 160 grams of the mother liquor from the batch crystallization described in Example 1 was combined with 2441.2 grams of the same fresh feed and subjected to evaporative crystallization at 10° C. The broth was evaporated to the point at which the average concentration of soluble inorganics (K, Na, and P) increased by a factor of 6.00 in the mother liquor, or filtrate, relative to that in the fresh feed and 1772.2 grams of distillate was recovered. After vacuum filtration, a methanol wash, and drying, 185.23 grams of a 85.9 wt % pure (anhydrous basis) KLG product was recovered corresponding to 41.8% KLG recovery. The composition of the resultant mother liquor is given in Table 2. Given the mother liquor from Example 1 was more underprotonated than the fresh feed (60.9% versus 87.5%), it is not surprising that the ratio of available protons to KLG was even lower in this mother liquor (43.5%). This underprotonation likely contributed to the poor KLG recovery and illustrates the shortcomings of relying solely on pH to control acidification of the carboxylate solution.

Example 3

After acidification to pH-2 with sulfuric acid, carbon treatment, and microfiltration to remove cells, carbon and other solids, the same broth used as the fresh feed in Examples 1 and 2 was further pretreated by contact with the hydrogen form of a cation exchange resin. The resultant broth had a composition given in Table 1, of which 3000.5 grams was subjected to evaporative crystallization at 10° C. The broth was evaporated to the point at which the phosphorus concentration increased by a factor of 4.90 in the mother liquor, or filtrate, relative to that in the feed and 2240 grams of distillate was recovered. After vacuum filtration, a methanol wash, and drying, 215.0 grams of a 88.1 wt % pure (anhydrous basis) KLG product was recovered corresponding to 52.6% KLG recovery. The composition of the mother liquor is given in Table 2. In contrast to Example 1, comparison of the ratio of available protons to KLG in the feed (112.1%) to that in the mother liquor (132.4%) reveals that the feed broth was overprotonated and became more so as KLG was crystallized. This was also reflected by the pH decrease from 1.8 in the feed to 0.44 in the mother liquor and the appearance of ascorbic acid, a by product of KLG decomposition, in the mother liquor (1.39 wt %). This example further illustrates the inadequacy of using pH as a measure of protonation as the fresh feed pH was the same (1.8) as in Example 1, although by charge balance the feed in Example 1 was underprotonated while in this case it was overprotonated.

Example 4

To simulate mother liquor recycle in a continuous crystallization process, 423.6 grams of the mother liquor from the batch crystallization described in Example 3 was combined with 2440.6 grams of the same fresh feed and subjected to evaporative crystallization at 10° C. The broth was evaporated to the point at which the phosphorus concentration increased by a factor of 8.63 in the mother liquor, or filtrate, relative to that in the fresh feed and 2000.7 grams of distillate was recovered. After vacuum filtration, a methanol wash, and drying, 300.88 grams of a 86.8 wt % pure (anhydrous basis) KLG product was recovered corresponding to 67.9% KLG recovery. The composition of the resultant mother liquor is given in Table 2. Given the mother liquor from Example 3 was more overprotonated than the fresh feed (132.4% versus 112.1%), it is not surprising that the ratio of available protons to KLG was even higher in this mother liquor (178.5%). KLG losses by decomposition were also higher as reflected by the increased ascorbic acid level in the mother liquor (2.28 wt %).

Example 5

To further simulate mother liquor recycle in a continuous crystallization process, 490 grams of the mother liquor from the batch crystallization described in Example 4 was combined with 2433.1 grams of the same fresh feed used in Examples 3 and 4 and subjected to evaporative crystallization at 10° C. The broth was evaporated to the point at which the phosphorus concentration increased by a factor of 11.76 in the mother liquor, or filtrate, relative to that in the fresh feed and 2000.8 grams of distillate was recovered. After vacuum filtration, a methanol wash, and drying, 285.53 grams of a 84.5 wt % pure (anhydrous basis) KLG product was recovered corresponding to 65.2% KLG recovery. The composition of the resultant mother liquor is given in Table 2. Given the mother liquor from Example 4 was even more overprotonated than the fresh feed (178.5% versus 112.1%), it is not surprising that the ratio of available protons to KLG was yet even higher in this mother liquor (203.2%). KLG losses by decomposition were also higher as reflected by the increased ascorbic acid level in the mother liquor (2.81 wt %).

Example 6

After microfiltration at pH~7 to remove cells, acidification to pH~2 with sulfuric acid, carbon treatment, and filtration to remove carbon and other solids, a broth was further pretreated by adding more sulfuric acid, filtration, and contact with the hydrogen form of a cation exchange resin. The additional sulfuric acid was intended to fully protonate the KLG and was based upon a $C^{13}$ NMR measurement of the degree of proton association with KLG in the broth. The resultant broth had a composition given in Table 1, of which 3000.2 grams was subjected to evaporative crystallization at 10° C. The broth was evaporated to the point at which the concentration of phosphorus increased by a factor of 6.32 in the mother liquor, or filtrate, relative to that in the feed and 2387.6 grams of distillate was recovered. After vacuum filtration, a methanol wash, and drying, 234.85 grams of a 87.4 wt % pure (anhydrous basis) KLG product was recovered corresponding to 76.9% KLG recovery. The composition of the mother liquor is given in Table 2. The combination of additional sulfuric acid and cation exchange led to overprotonation as reflected by the ratio of available protons to KLG in the feed of 136.6% and it became more so as KLG was crystallized as the ratio increased to 261.4% in the mother liquor. Again, there was evidence for KLG decomposition as the mother liquor contained 2.85 wt % ascorbic acid.

Example 7

To simulate mother liquor recycle in a continuous crystallization process, 217.7 grams of the mother liquor from the batch crystallization described in Example 6 was combined with 2640.3 grams of the same fresh feed and subjected to evaporative crystallization at 10° C. The broth was evaporated to the point at which the phosphorus concentration increased by a factor of 14.93 in the mother liquor, or filtrate, relative to that in the fresh feed and 2239.9 grams of distillate was recovered. The composition of the resultant mother liquor is given in Table 2. Given the mother liquor from Example 6 was more overprotonated than the fresh feed (261.4% versus 136.6%), it is not surprising that both the ratio of available protons to KLG (300.2%) and ascorbic acid levels (3.14 wt %) were even higher in this mother liquor.

Example 8

The feed broth for this example was pretreated the same as that described in Example 6 except yet even more sulfuric acid was added before cation exchange. The resultant broth had a composition given in Table 1, of which 3000.4 grams was subjected to evaporative crystallization at 10° C. The broth was evaporated to the point at which the phosphorus concentration increased by a factor of 6.16 in the mother liquor, or filtrate, relative to that in the feed and 2317.6 grams of distillate was recovered. After vacuum filtration, a methanol wash, and drying, 230.42 grams of a 84.9 wt % pure (anhydrous basis) KLG product was recovered corresponding to 59.9% KLG recovery. The composition of the mother liquor is given in Table 2. The combination of extra sulfuric acid and cation exchange led to even greater overprotonation as reflected by the ratio of available protons to KLG in the feed of 143.8% and it became more so as KLG was crystallized as the ratio increased to 329.8% in the mother liquor. Again, there was evidence for KLG decomposition as the mother liquor contained 2.0 wt % ascorbic acid.

Example 9

To simulate mother liquor recycle in a continuous crystallization process, 323.6 grams of the mother liquor from the batch crystallization described in Example 8 was combined with 2580.1 grams of the same fresh feed and subjected to evaporative crystallization at 10° C. The broth was evaporated to the point at which the phosphorus concentration increased by a factor of 10.25 in the mother liquor, or filtrate, relative to that in the fresh feed and 2189.2 grams of distillate was recovered. After vacuum filtration, a methanol wash, and drying, 242.54 grams of a 89.6 wt % pure (anhydrous basis) KLG product was recovered corresponding to 67.2% KLG recovery. The composition of the resultant mother liquor is given in Table 2. Given the mother liquor from Example 8 was more overprotonated than the fresh feed (329.8% versus 143.8%), it is not surprising that the ratio of available protons to KLG was even higher in this mother liquor (604.2%). KLG losses by decomposition were also higher as reflected by the increased ascorbic acid level in the mother liquor (3.37 wt %).

Example 10

To further simulate mother liquor recycle in a continuous crystallization process, 213.9 grams of the mother liquor from the batch crystallization described in Example 9 was combined with 2510.3 grams of the same fresh feed used in Examples 8 and 9 and subjected to evaporative crystallization at 10° C. The broth was evaporated to the point at which the phosphorus concentration increased by a factor of 8.95 in the mother liquor, or filtrate, relative to that in the fresh feed and 2121.7 grams of distillate was recovered. After vacuum filtration, a methanol wash, and drying, 242.21 grams of a 86.7 wt % pure (anhydrous basis) KLG product was recovered corresponding to 71.3% KLG recovery. The composition of the resultant mother liquor is given in Table 2. Because this broth was not concentrated by evaporation as much as that in Example 9, the ratio of available protons to KLG in the mother liquor was somewhat lower (503.1% versus 604.2%). It was clearly overprotonated, however, with 3.21 wt % of the KLG decomposition product ascorbic acid in the mother liquor.

Example 11

After acidification to pH~2 with sulfuric acid, carbon treatment, and microfiltration to remove cells, carbon and other solids, the same broth used as the fresh feed in Examples 1 and 2 was further pretreated by adding more sulfuric acid, filtration, and contact with the hydrogen form of a cation exchange resin. The additional sulfuric acid was beyond that required to fully protonate the KLG based upon a $C^{13}$ NMR measurement of the degree of proton association with KLG in the broth. The resultant broth had a composition given in Table 1, of which 3004 grams was subjected to evaporative crystallization at 10° C. The broth was evaporated to the point at which the phosphorus concentration increased by a factor of 4.02 in the mother liquor, or filtrate, relative to that in the feed and 2133.4 grams of distillate was recovered. After vacuum filtration, a methanol wash, and drying, 205.27 grams of a 86.5 wt % pure (anhydrous basis) KLG product was recovered corresponding to 48.1% KLG recovery. The composition of the mother liquor is given in Table 2. The combination of additional sulfuric acid and cation exchange led to overprotonation as reflected by the ratio of available protons to KLG in the feed of 141.3% and it became more so as KLG was crystallized as the ratio increased to 215.5% in the mother liquor. Again, there was evidence for KLG decomposition as the mother liquor contained 1.35 wt % ascorbic acid.

Example 12

To simulate mother liquor recycle in a continuous crystallization process, 590 grams of the mother liquor from the batch crystallization described in Example 11 was combined with 2610.1 grams of the same fresh feed and subjected to evaporative crystallization at 10° C. The broth was evaporated to the point at which the phosphorus concentration increased by a factor of 5.90 in the mother liquor, or filtrate, relative to that in the fresh feed and 2075.2 grams of distillate was recovered. After vacuum filtration, a methanol wash, and drying, 250.66 grams of a 88.2 wt % pure (anhydrous basis) KLG product was recovered corresponding to 51.8% KLG recovery. The composition of the resultant mother liquor is given in Table 2. Given the mother liquor from Example 11 was more overprotonated than the fresh feed (215.5% versus 141.3%), it is not surprising that the ratio of available protons to KLG was even higher in this mother liquor (288.8%). KLG losses by decomposition were also higher as reflected by the increased ascorbic acid level in the mother liquor (2.12 wt %).

Example 13

To further simulate mother liquor recycle in a continuous crystallization process, 680 grams of the mother liquor from the batch crystallization described in Example 12 was combined with 2450.2 grams of the same fresh feed used in Examples 11 and 12 and subjected to evaporative crystallization at 10° C. The broth was evaporated to the point at which the phosphorus concentration increased by a factor of 11.91 in the mother liquor, or filtrate, relative to that in the fresh feed and 2210.4 grams of distillate was recovered. After vacuum filtration, a methanol wash, and drying, 344.82 grams of a 82.5 wt % pure (anhydrous basis) KLG product was recovered corresponding to 69.4% KLG recovery. The composition of the resultant mother liquor is given in Table 2. The high degree of concentration by evaporation and the overprotonated feeds combined to lead to a very high ratio of available protons to KLG of 606.4% and a high ascorbic acid level of 4.87 wt % in this mother liquor.

Example 14

After microfiltration at pH~7 to remove cells, acidification to pH~2 with sulfuric acid, carbon treatment, and filtration to remove carbon and other solids, a broth was further pretreated by contact with the hydrogen form of a cation exchange resin. The resultant broth had a composition given in Table 1, of which 3000.1 grams was subjected to evaporative crystallization at 10° C. The broth was evaporated to the point at which the concentration of phosphorus increased by a factor of 5.03 in the mother liquor, or filtrate, relative to that in the feed and 2236.7 grams of distillate was recovered. After vacuum filtration, a methanol wash, and drying, 100.56 grams of a 89.4 wt % pure (anhydrous basis) KLG product was recovered corresponding to 36.1% KLG recovery. The composition of the mother liquor is given in Table 2. The cation exchange led to slight overprotonation as reflected by the ratio of available protons to KLG in the feed of 112.7% and it became only slightly more so during crystallization as the ratio increased to 119.8% in the mother liquor. KLG decomposition at these relatively mild conditions was minimal as reflected by the low ascorbic acid level of 0.53 wt % in this mother liquor. Again, pH was a poor measure of protonation as it decreased from 1.8 in the feed to 0.4 in the mother liquor much like Example 3 while both overprotonation of the mother liquor as determined by charge balance (119.8% versus 132.4%) and KLG decomposition as indicated by ascorbic acid level (0.53 versus 1.39 wt %) were lower in this example.

Example 15

To simulate mother liquor recycle in a continuous crystallization process, 511.6 grams of the mother liquor from the batch crystallization described in Example 14 was combined with 2840.2 grams of the same fresh feed and subjected to evaporative crystallization at 10° C. The broth was evaporated to the point at which the phosphorus concentration increased by a factor of 7.03 in the mother liquor, or filtrate, relative to that in the fresh feed and 2217.1 grams of distillate was recovered. After vacuum filtration, a methanol wash, and drying, 249.77 grams of a 88.9 wt % pure (anhydrous basis) KLG product was recovered corresponding to 59.7% KLG recovery. The composition of the resultant mother liquor is given in Table 2. Because the protonation level of the fresh feed (112.7%) and the mother liquor feed (119.8%) were similar and the feed was not highly concentrated, the ratio of available protons to KLG in the mother liquor increased only modestly to 132.6% in this example. Likewise, the mother liquor pH (0.35) and ascorbic acid level (0.93 wt %) were indicative of only modest overprotonation.

Example 16

To further simulate mother liquor recycle in a continuous crystallization process, 741.1 grams of the mother liquor from the batch crystallization described in Example 15 was combined with 2540.1 grams of the same fresh feed used in Examples 14 and 15 and subjected to evaporative crystallization at 10° C. The broth was evaporated to the point at which the phosphorus concentration increased by a factor of 9.07 in the mother liquor, or filtrate, relative to that in the fresh feed and 2137.1 grams of distillate was recovered. After vacuum filtration, a methanol wash, and drying, 206.39 grams of a 89.7 wt % pure (anhydrous basis) KLG product was recovered corresponding to 49.2% KLG recovery. The composition of the resultant mother liquor is given in Table 2. Overprotonation was higher in this example than in Example 15 as indicated by the ratio of available protons to KLG in the mother liquor (146.8%), the ascorbic acid level (1.67 wt %), and the mother liquor pH (0.15).

Example 17

After acidification to pH~2 with sulfuric acid, carbon treatment, and microfiltration to remove cells, carbon and other solids, the same broth used as the fresh feed in Examples 1 and 2 was further pretreated by adding more sulfuric acid and filtration. The additional sulfuric acid was that required to fully protonate the KLG based upon a $C^{13}$ NMR measurement of the degree of proton association with KLG in the broth. The resultant broth had a composition given in Table 1, of which 3000 grams was subjected to evaporative crystallization at 10° C. The broth was evaporated to the point at which the average concentration of soluble inorganics (K, Na, Mg, and P) increased by a factor of 8.76 in the mother liquor, or filtrate, relative to that in the feed and 2304.1 grams of distillate was recovered. After vacuum filtration, a methanol wash, and drying, 301.58 grams of a 86.6 wt % pure (anhydrous basis) KLG product was recovered corresponding to 65.8% KLG recovery. The composition of the mother liquor is given in Table 2. The additional sulfuric acid alone led to overprotonation as reflected by the ratio of available protons to KLG in the feed of 110.7% and it became more so as KLG was crystallized as the ratio increased to 161.2% in the mother liquor. This example further illustrates the shortcoming of using pH as a measure of protonation as the pH of the feed in this example was 1.41 while the pH for the feeds in Examples 3 and 14 were both 1.8 despite having similar ratios of available protons to KLG as determined by charge balance (Table 1).

Example 18

To simulate mother liquor recycle in a continuous crystallization process, 184.1 grams of the mother liquor from the batch crystallization described in Example 17 was combined with 3000.9 grams of the same fresh feed and subjected to evaporative crystallization at 10° C. The broth was evaporated to the point at which the average concentration of soluble inorganics (K, Na, Mg, and P) increased by a factor of 8.03 in the mother liquor, or filtrate, relative to that in the fresh feed and 2441.5 grams of distillate was recovered. After vacuum filtration, a methanol wash, and drying, 306.81 grams of a 88.7 wt % pure (anhydrous basis) KLG product was recovered corresponding to 62.4% KLG recovery. The composition of the resultant mother liquor is given in Table 2. Because the feed was a little less concentrated by evaporation as in Example 17, the ratio of available protons to KLG in the mother liquor was slightly lower (148.4% versus 161.2%) in this example.

Example 19

To further simulate mother liquor recycle in a continuous crystallization process, 466.2 grams of the mother liquor from the batch crystallization described in Example 18 was combined with 2663.1 grams of the same fresh feed used in Examples 17 and 18 and subjected to evaporative crystallization at 10° C. The broth was evaporated to the point at which the average concentration of soluble inorganics (K, Na, Mg, and P) increased by a factor of 10.78 in the mother liquor, or filtrate, relative to that in the fresh feed and 2165.3 grams of distillate was recovered. After vacuum filtration, a methanol wash, and drying, 341.85 grams of a 86.7 wt % pure (anhydrous basis) KLG product was recovered corresponding to 64.8% KLG recovery. The composition of the resultant mother liquor is given in Table 2. Consistent with the higher degree of concentration by evaporation, overprotonation was somewhat higher in this example than in Examples 17 and 18 as indicated by the ratio of available protons to KLG in the mother liquor (172.7%).

Example 20

After microfiltration at pH~7 to remove cells, acidification to pH~2 with sulfuric acid, carbon treatment, and filtration to remove carbon and other solids, a broth was further pretreated by adding more sulfuric acid and filtration. The additional sulfuric acid was that required to fully protonate the KLG based upon a $C^{13}$ NMR measurement of the degree of proton association with KLG in the broth. The resultant broth had a composition given in Table 1, of which 3000.3 grams was subjected to evaporative crystallization at 10° C. The broth was evaporated to the point at which the average concentration of soluble inorganics (K, Na, Mg, and P) increased by a factor of 8.77 in the mother liquor, or filtrate, relative to that in the feed and 2302.1 grams of distillate was recovered. After vacuum filtration, a methanol wash, and drying, 250.25 grams of a 84.4 wt % pure (anhydrous basis) KLG product was recovered corresponding to 57.0% KLG recovery. The composition of the mother liquor is given in Table 2. The additional sulfuric acid alone led to overprotonation as reflected by the ratio of available protons to KLG in the feed of 110.0% and it became more so as KLG was crystallized as the ratio increased to 151.1% in the mother liquor. Decreasing pH from 1.44 in the fresh feed to 0.63 in the mother liquor was also indicative of this increasing acidification.

Comparison of these results with those from Example 17 reveals that despite starting from similar protonation levels, concentrating by the same factor, and obtaining the same KLG solubility in the mother liquor, both KLG recovery and mother liquor protonation were lower in this example than in Example 17. This reflects the lower KLG concentration in the pretreated feed for this example and can be rationalized using simple mass-balance models.

Example 21

To simulate mother liquor recycle in a continuous crystallization process, 260.9 grams of the mother liquor from the batch crystallization described in Example 20 was combined with 3000.1 grams of the same fresh feed and subjected to evaporative crystallization at 10° C. The broth was evaporated to the point at which the average concentration of soluble inorganics (K, Na, Mg, and P) increased by a factor of 11.38 in the mother liquor, or filtrate, relative to that in the fresh feed and 2400 grams of distillate was recovered. After vacuum filtration, a methanol wash, and drying, 323.37 grams of a 86.6 wt % pure (anhydrous basis) KLG product was recovered corresponding to 65.7% KLG recovery. The composition of the resultant mother liquor is given in Table 2. The overprotonated feed and relatively high degree of concentration led to a higher ratio (176.5%) of available protons to KLG and lower pH (0.57) in this mother liquor compared to that from Example 20.

Example 22

To further simulate mother liquor recycle in a continuous crystallization process, 360 grams of the mother liquor from the batch crystallization described in Example 21 was combined with 2490 grams of the same fresh feed used in Examples 20 and 21 and subjected to evaporative crystallization at 10IC. The broth was evaporated to the point at which the average concentration of soluble inorganics (K, Na, Mg, and P) increased by a factor of 12.25 in the mother liquor, or filtrate, relative to that in the fresh feed and 2090.9 grams of distillate was recovered. After vacuum filtration, a methanol wash, and drying, 299.46 grams of a 84.8 wt % pure (anhydrous basis) KLG product was recovered corresponding to 67.3% KLG recovery. The composition of the resultant mother liquor is given in Table 2. Consistent with the slightly higher degree of concentration by evaporation, overprotonation was a little higher in this example than in Examples 20 and 21 as indicated by the ratio of available protons to KLG in the mother liquor (181.0%).

Example 23

After microfiltration at pH~7 to remove cells, acidification to pH~2 with sulfuric acid, carbon treatment, and filtration to remove carbon and other solids, the same broth used to prepare the fresh feeds in Examples 6–10, 14–16, and 20–22 was crystallized without further pretreatment. This underacidified broth had a composition given in Table 1, of which 3000 grams was subjected to evaporative crystallization at 10° C. The broth was evaporated to the point at which the average concentration of soluble inorganics (K, Na, Mg, and P) increased by a factor of 7.73 in the mother liquor, or filtrate, relative to that in the feed and 2225.6 grams of distillate was recovered. After vacuum filtration, a methanol wash, and drying, 237.27 grams of a 82.0 wt % pure (anhydrous basis) KLG product was recovered corresponding to 53.5% KLG recovery. The composition of the mother liquor is given in Table 2. Comparison of the ratio of available protons to KLG as determined by charge balance in the feed (89.3%) to that in the mother liquor (68.6%) reveals that the feed broth was underprotonated and became even more proton deficient as KLG was crystallized.

Example 24

To simulate mother liquor recycle in a continuous crystallization process, 225.8 grams of the mother liquor from the batch crystallization described in Example 23 was combined with 2800.6 grams of the same fresh feed and subjected to evaporative crystallization at 10° C. The broth was evaporated to the point at which the average concentration of soluble inorganics (K, Na, Mg, and P) increased by a factor of 9.77 in the mother liquor, or filtrate, relative to that in the fresh feed and 2263.9 grams of distillate was recovered. After vacuum filtration, a methanol wash, and drying, 307.96 grams of a 80.9 wt % pure (anhydrous basis) KLG product was recovered corresponding to 60.9% KLG recovery. The composition of the resultant mother liquor is given in Table 2. The increased concentration factor and addition of even further underprotonated mother liquor to the fresh feed led to a greater degree of proton deficiency in this example as reflected by both the ratio of available protons to KLG (63.0% versus 68.6%) and pH (2.18 versus 2.14) when compared to Example 23.

Example 25

To further simulate mother liquor recycle in a continuous crystallization process, 234.2 grams of the mother liquor from the batch crystallization described in Example 24 was combined with 2800.1 grams of the same fresh feed used in Examples 23 and 24 and subjected to evaporative crystallization at 10° C. The broth was evaporated to the point at which the average concentration of soluble inorganics (K, Na, Mg, and P) increased by a factor of 10.32 in the mother liquor, or filtrate, relative to that in the fresh feed and 2250 grams of distillate was recovered. After vacuum filtration, a methanol wash, and drying, 340.16 grams of a 81.2 wt % pure (anhydrous basis) KLG product was recovered corresponding to 66.3% KLG recovery. The composition of the resultant mother liquor is given in Table 2. Again, this mother liquor was underprotonated as reflected by both its ratio of available protons to KLG (63.4%) and pH (2.23).

Example 26

The same broth used as the fresh feed in Examples 23–25 was further pretreated by adding more sulfuric acid, filtration, and contact with the hydrogen form of a cation exchange resin much like the fresh feed used in Examples 6 and 7. The additional sulfuric acid was intended to fully protonate the KLG and was based upon a $C^{13}$ NMR measurement of the degree of proton association with KLG in the broth. The resultant broth had a composition given in Table 1, of which 3000 grams was subjected to evaporative crystallization at 10° C. The broth was evaporated to the point at which the average concentration of soluble inorganics (K, Na, and P) increased by a factor of 5.76 in the mother liquor, or filtrate, relative to that in the feed and 2224.1 grams of distillate was recovered. After vacuum filtration, a methanol wash, and drying, 211.06 grams of a 90.1 wt % pure (anhydrous basis) KLG product was recovered corresponding to 51.6% KLG recovery. The composition of the mother liquor is given in Table 2. The combination of additional sulfuric acid and cation exchange led to overprotonation as reflected by the ratio of available protons to KLG in the feed of 133.3% and it became more so as KLG was crystallized as the ratio increased to 239.3% in the mother liquor.

Example 27

To simulate mother liquor recycle in a continuous crystallization process, 407.6 grams of the mother liquor from the batch crystallization described in Example 26 was combined with 2959.6 grams of the same fresh feed and subjected to evaporative crystallization at 10° C. The broth was evaporated to the point at which the average concentration of soluble inorganics (K, Na, and P) increased by a factor of 9.52 in the mother liquor, or filtrate, relative to that in the fresh feed and 2158.6 grams of distillate was recovered. After vacuum filtration, a methanol wash, and drying, 267.41 grams of a 86.5 wt % pure (anhydrous basis) KLG product was recovered corresponding to 53.5% KLG recovery. The composition of the resultant mother liquor is given in Table 2. Compared to Example 26, the increased concentration factor and addition of even further overprotonated mother liquor to the fresh feed led to a greater surplus of protons as reflected by the ratio of available protons to KLG (377.1% versus 239.3%). Again, there was evidence for KLG decomposition as the mother liquor contained 1.4 wt % ascorbic acid.

Example 28

To further simulate mother liquor recycle in a continuous crystallization process, 329.5 grams of the mother liquor from the batch crystallization described in Example 27 was combined with 2519.5 grams of the same fresh feed used in Examples 26 and 27 and subjected to evaporative crystallization at 10° C. The broth was evaporated to the point at which the average concentration of soluble inorganics (K, Na, and P) increased by a factor of 10.32 in the mother liquor, or filtrate, relative to that in the fresh feed and 2053.4 grams of distillate was recovered. After vacuum filtration, a methanol wash, and drying, 247.18 grams of a 86.8 wt % pure (anhydrous basis) KLG product was recovered corresponding to 60.2% KLG recovery. The composition of the resultant mother liquor is given in Table 2. Again, this mother liquor was overprotonated as reflected by both its ratio of available protons to KLG (395.2%) and ascorbic acid content (2.02 wt %).

Example 29

After acidification to pH~2 with sulfuric acid, carbon treatment, and microfiltration to remove cells, carbon and other solids, the same broth used as the fresh feed in Examples 1 and 2 was further pretreated by contact with the hydrogen form of a cation exchange resin. The resultant broth had a composition given in Table 1, of which 3000.2 grams was subjected to evaporative crystallization at 10° C. The broth was evaporated to the point at which the average concentration of soluble inorganics (K, Na, and P) increased by a factor of 5.65 in the mother liquor, or filtrate, relative to that in the feed and 2231.3 grams of distillate was recovered. After vacuum filtration, a methanol wash, and drying, 261.28 grams of a 88.8 wt % pure (anhydrous basis) KLG product was recovered corresponding to 69.4% KLG recovery. The composition of the mother liquor is given in Table 2. The cation exchange led to slight overprotonation as reflected by the ratio of available protons to KLG in the feed of 109.0% and it became more so as KLG was crystallized as the ratio increased to 126.9% in the mother liquor.

Example 30

To simulate mother liquor recycle in a continuous crystallization process, 350.3 grams of the mother liquor from the batch crystallization described in Example 29 was combined with 2560 grams of the same fresh feed and subjected to evaporative crystallization at 10° C. The broth was evaporated to the point at which the average concentration of soluble inorganics (K, Na, and P) increased by a factor of 10.03 in the mother liquor, or filtrate, relative to that in the fresh feed and 2167.8 grams of distillate was recovered. After vacuum filtration, a methanol wash, and drying, 294.04 grams of a 88.8 wt % pure (anhydrous basis) KLG product was recovered corresponding to 71.9% KLG recovery. The composition of the resultant mother liquor is given in Table 2. The overprotonated feed and relatively high degree of concentration led to a higher ratio (159.9%) of available protons to KLG in this mother liquor compared to that from Example 29.

Example 31

To further simulate mother liquor recycle in a continuous crystallization process, 289 grams of the mother liquor from the batch crystallization described in Example 30 was combined with 2522.8 grams of the same fresh feed used in Examples 29 and 30 and subjected to evaporative crystallization at 10° C. The broth was evaporated to the point at which the average concentration of soluble inorganics (K, Na, and P) increased by a factor of 13.23 in the mother liquor, or filtrate, relative to that in the fresh feed and 2116.5 grams of distillate was recovered. After vacuum filtration, a methanol wash, and drying, 317.18 grams of a 81.1 wt % pure (anhydrous basis) KLG product was recovered corresponding to 76.9% KLG recovery. The composition of the resultant mother liquor is given in Table 2. Again, this mother liquor was overprotonated as reflected by its ratio of available protons to KLG (177.4%).

Example 32

The same broth used as the fresh feed in Examples 23–25 was further pretreated by adding more sulfuric acid, filtration, and contact with the hydrogen form of a cation exchange resin much like the fresh feed used in Examples 6, 7 and 26–28. The additional sulfuric acid was intended to fully protonate the KLG and was based upon a $C^{13}$ NMR measurement of the degree of proton association with KLG in the broth. The resultant broth had a composition given in Table 1, of which 3100.4 grams was subjected to evaporative crystallization at 10° C. The broth was evaporated to the point at which the average concentration of soluble inorganics (Na and P) increased by a factor of 5.95 in the mother liquor, or filtrate, relative to that in the feed and 2341 grams of distillate was recovered. After vacuum filtration, a methanol wash, and drying, 246.84 grams of a 88.4 wt % pure (anhydrous basis) KLG product was recovered corresponding to 61.4% KLG recovery. The composition of the mother liquor is given in Table 2. The combination of additional sulfuric acid and cation exchange led to overprotonation as reflected by the ratio of available protons to KLG in the feed of 133.7% and it became more so as KLG was crystallized as the ratio increased to 242.7% in the mother liquor.

Example 33

To simulate mother liquor recycle in a continuous crystallization process, 381.7 grams of the mother liquor from the batch crystallization described in Example 32 was combined with 2663.9 grams of the same fresh feed and subjected to evaporative crystallization at 10° C. The broth was evaporated to the point at which the average concentration of soluble inorganics (Na and P) increased by a factor of 10.94 in the mother liquor, or filtrate, relative to that in the fresh feed and 2231.1 grams of distillate was recovered. After vacuum filtration, a methanol wash, and drying, 299.63 grams of a 85.7 wt % pure (anhydrous basis) KLG product was recovered corresponding to 70.0% KLG recovery. The composition of the resultant mother liquor is given in Table 2. Compared to Example 32, the increased concentration factor and addition of even further overprotonated mother liquor to the fresh feed led to a greater surplus of protons as reflected by the ratio of available protons to KLG (448.6% versus 242.7%). Again, there was evidence for KLG decomposition as the mother liquor contained 1.4 wt % ascorbic acid.

Example 34

To further simulate mother liquor recycle in a continuous crystallization process, 308.3 grams of the mother liquor from the batch crystallization described in Example 33 was combined with 2600 grams of the same fresh feed used in Examples 32 and 33 and subjected to evaporative crystallization at 10° C. The broth was evaporated to the point at which the average concentration of soluble inorganics (Na and P) increased by a factor of 12.71 in the mother liquor, or filtrate, relative to that in the fresh feed and 2189.9 grams of distillate was recovered. After vacuum filtration, a methanol wash, and drying, 318.36 grams of a 80.5 wt % pure (anhydrous basis) KLG product was recovered corresponding to 76.4% KLG recovery. The composition of the resultant mother liquor is given in Table 2. Again, this mother liquor was overprotonated as reflected by both its ratio of available protons to KLG (463.1%) and ascorbic acid content (2.65 wt %).

Analysis of the crystallization results from Examples 1–34 shows the impact of protonation on KLG solubility and decomposition. As shown in FIG. 2, KLG solubility decreased as the ratio of available protons to KLG in the mother liquor increased. Given recovery via crystallization improves as the solubility is reduced, these results suggest protonation should be as high as possible in the crystallizer to maximize recovery. However, as shown in FIG. 3, KLG decomposition as measured by ascorbic acid content also increased as the ratio of available protons to KLG in the mother liquor increased. Examples 35–44 reflect initial attempts to moderate the effects of feed protonation on KLG crystallization using anion exchange, careful acidification, and buffering.

Example 35

After acidification to pH~2 with sulfuric acid, carbon treatment, and microfiltration to remove cells, carbon and other solids, the same broth used as the fresh feed in Examples 1 and 2 was further pretreated by contact with the hydrogen form of a cation exchange resin followed by contact with the hydroxyl form of an anion exchange resin. The resultant broth had a composition given in Table 1, of which 9013.5 grams was subjected to evaporative crystallization at 10° C. The broth was evaporated to the point at which the average concentration of soluble inorganics (Ca, K, Na, and Mg) increased by a factor of 4.01 in the mother liquor, or filtrate, relative to that in the feed and 6497.7 grams of distillate was recovered. After vacuum filtration, two water washes, and drying, 209.30 grams of a 88.2 wt % pure (anhydrous basis) KLG product was recovered corresponding to 24.7% KLG recovery. The composition of the mother liquor is given in Table 2. While the anion exchange was very effective in removing the inorganic anions (i.e., P, S, and Cl), the cation exchange was incomplete leaving some inorganic cations (i.e., Ca, K, Na, and Mg) in the feed broth. As a result, the pretreated feed was underprotonated as reflected by the ratio of available protons to KLG in the feed of 95.2% which changed very little upon crystallization (96.9%) due to the relatively low degree of concentration and KLG crystallization.

Example 36

To simulate mother liquor recycle in a continuous crystallization process, 2188.3 grams of the mother liquor from the batch crystallization described in Example 35 was subjected to further evaporative crystallization at 10° C. The broth was evaporated to the point at which the average concentration of soluble inorganics (Ca, K, Na, and Mg) increased by a factor of 16.37 in the mother liquor, or filtrate, relative to that in the fresh feed and 1141.3 grams of distillate was recovered. After vacuum filtration, two water washes, and drying, 499.03 grams of a 78.8 wt % pure (anhydrous basis) KLG product was recovered corresponding to 71.4% KLG recovery. The composition of the resultant mother liquor is given in Table 2. Compared to Example 35, the increased concentration led to a greater deficit of protons as reflected by both the ratio of available protons to KLG (88.5% versus 96.9%) and the mother liquor pH (1.8 versus 1.49). This example illustrates a shortcoming of simply following cation exchange with anion exchange as a means of properly protonating the solution. Unless the ion exchange steps are nearly perfectly performed, the resultant solution may still be improperly protonated.

Example 37

After acidification to pH~2 with sulfuric acid, carbon treatment, and microfiltration to remove cells, carbon and other solids, the same broth used as the fresh feed in Example s 1 and 2 was further pretreated by contact with the hydrogen form of a cation exchange resin followed by contact with the hydroxyl form of an anion exchange resin much like Example 35. The resultant broth had a composition given in Table 1, of which 8999.9 grams was subjected to evaporative crystallization at 10° C. The broth was evaporated to the point at which the average concentration of soluble inorganics (Ca, K, Na, and Mg) increased by a factor of 3.92 in the mother liquor, or filtrate, relative to that in the feed and 6450.1 grams of distillate was recovered. After vacuum filtration, two water washes, and drying, 203.59 grams of a 86.8 wt % pure (anhydrous basis) KLG product was recovered corresponding to 23.4% KLG recovery. The composition of the mother liquor is given in Table 2. Again, while the anion exchange was very effective in removing the inorganic anions (i.e., P, S, and Cl), the cation exchange was incomplete leaving some inorganic cations (i.e., Ca, K, Na, and Mg) in the feed broth. As a result, the pretreated feed was underprotonated as reflected by the ratio of available protons to KLG in the feed of 95.3% which changed very little upon crystallization (97.1%) due to the relatively low degree of concentration and KLG crystallization.

Example 38

To simulate mother liquor recycle in a continuous crystallization process, 2211.4 grams of the mother liquor from the batch crystallization described in Example 37 was subjected to further evaporative crystallization at 10° C. The broth was evaporated to the point at which the average concentration of soluble inorganics (Ca, K, Na, and Mg) increased by a factor of 16.57 in the mother liquor, or filtrate, relative to that in the fresh feed and 1161.6 grams of distillate was recovered. After vacuum filtration, two water washes, and drying, 485.3 grams of a 78.8 wt % pure (anhydrous basis) KLG product was recovered corresponding to 72.6% KLG recovery. The composition of the resultant mother liquor is given in Table 2. Compared to Example 37, the increased concentration led to a greater deficit of protons as reflected by both the ratio of available protons to KLG (89.0% versus 97.1%) and the mother liquor pH (1.83 versus 1.5). Again, this example illustrates a shortcoming of simply following cation exchange with anion exchange as a means of properly protonating the solution.

Example 39

After acidification to pH~2 with sulfuric acid, carbon treatment, and microfiltration to remove cells, carbon and other solids, the same broth used as the fresh feed in Examples 1 and 2 was further pretreated by adding more sulfuric acid and filtration much like Example 17. The additional sulfuric acid was that required to fully protonate the KLG based upon a $C^{13}$ NMR measurement of the degree of proton association with KLG in the broth. The resultant broth had a composition given in Table 1, of which 9001.6 grams was subjected to evaporative crystallization at 10 °C. The broth was evaporated to the point at which the average concentration of soluble inorganics (K, Na, Mg, P, and Cl) increased by a factor of 5.05 in the mother liquor, or filtrate, relative to that in the feed and 6391.8 grams of distillate was recovered. After vacuum filtration, two water washes, and drying, 797.4 grams of a 79.6 wt % pure (anhydrous basis) KLG product was recovered corresponding to 58.4% KLG recovery. The composition of the mother liquor is given in Table 2. The additional sulfuric acid alone led to overprotonation as reflected by the ratio of available protons to KLG in the feed of 111.4% and it became more so as KLG was crystallized as the ratio increased to 130.5% in the mother liquor.

Example 40

To simulate mother liquor recycle in a continuous crystallization process, 1226 grams of the mother liquor from the batch crystallization described in Example 39 was subjected to further evaporative crystallization at 10° C. The broth was evaporated to the point at which the average concentration of soluble inorganics (K, Na, Mg, P, and Cl) increased by a factor of 12.17 in the mother liquor, or filtrate, relative to that in the fresh feed and 491.7 grams of distillate was recovered. After vacuum filtration, two water washes, and drying, 232.2 grams of a 70.4 wt % pure (anhydrous basis) KLG product was recovered corresponding to 57.6% KLG recovery. The composition of the resultant mother liquor is given in Table 2. Compared to Example 39, the increased concentration led to a greater surplus of protons as reflected by both the ratio of available protons to KLG (199.1% versus 130.5%) and the mother liquor pH (0.46 versus 0.91). There was also evidence for KLG decomposition as the ascorbic acid level in the mother liquor was 2.41 wt %.

Example 41

After acidification to pH~2 with sulfuric acid, carbon treatment, and microfiltration to remove cells, carbon and other solids, the same broth used as the fresh feed in Examples 1 and 2 was further pretreated by adding more sulfuric acid and filtration much like Examples 17 and 39. The additional sulfuric acid was that required to fully protonate the KLG based upon a $C^{13}$ NMR measurement of the degree of proton association with KLG in the broth. The resultant broth had a composition given in Table 1, of which 9000 grams was subjected to evaporative crystallization at 10° C. The broth was evaporated to the point at which the average concentration of soluble inorganics (K, Na, Mg, P, and Cl) increased by a factor of 4.76 in the mother liquor, or filtrate, relative to that in the feed and 6346.1 grams of distillate was recovered. After vacuum filtration, two water washes, and drying, 767.1 grams of a 87.8 wt % pure (anhydrous basis) KLG product was recovered corresponding to 62.2% KLG recovery. The composition of the mother liquor is given in Table 2. The additional sulfuric acid alone led to overprotonation as reflected by the ratio of available protons to KLG in the feed of 110.2% and it became more so as KLG was crystallized as the ratio increased to 127.3% in the mother liquor.

Example 42

To simulate mother liquor recycle in a continuous crystallization process, 1458.4 grams of the mother liquor from the batch crystallization described in Example 41 was subjected to further evaporative crystallization at 10° C. The broth was evaporated to the point at which the average concentration of soluble inorganics (K, Na, Mg, P, and Cl) increased by a factor of 12.13 in the mother liquor, or filtrate, relative to that in the fresh feed and 671.0 grams of distillate was recovered. After vacuum filtration, two water washes, and drying, 293.4 grams of a 73.0 wt % pure (anhydrous basis) KLG product was recovered corresponding to 65.7% KLG recovery. The composition of the resultant mother liquor is given in Table 2. Compared to Example 41, the increased concentration led to a greater surplus of protons as reflected by both the ratio of available protons to KLG (193.5% versus 127.3%) and the mother liquor pH (0.71 versus 1.05). There was also evidence for KLG decomposition as the ascorbic acid level in the mother liquor was 1.82 wt %.

Example 43

The same broth used as the fresh feed in Examples 23–25 was further pretreated by contact with the hydrogen form of a cation exchange resin much like the fresh feed used in Examples 14–16. Sodium sulfate salt was subsequently added to the broth in an attempt to moderate the increasing proton concentration upon evaporation. The resultant broth had a composition given in Table 1, of which 9000.2 grams was subjected to evaporative crystallization at 10° C. The broth was evaporated to the point at which the average concentration of soluble inorganics (Na and P) increased by a factor of 6.21 in the mother liquor, or filtrate, relative to that in the feed and 6858.7 grams of distillate was recovered. After vacuum filtration, two water washes, and drying, 720.1 grams of a 86.6 wt % pure (anhydrous basis) KLG product was recovered corresponding to 67.4% KLG recovery. The composition of the mother liquor is given in Table 2. Sodium sulfate addition was ineffective in reducing the overprotonation resulting from cation exchange as the ratio of available protons to KLG in the feed was 110.1% and increased to 134.8% in the mother liquor while the pH decreased from 1.55 to 0.65.

Example 44

To simulate mother liquor recycle in a continuous crystallization process, 1110.7 grams of the mother liquor from the batch crystallization described in Example 43 was subjected to further evaporative crystallization at 10° C. The broth was evaporated to the point at which the average concentration of soluble inorganics (Na and P) increased by a factor of 14.24 in the mother liquor, or filtrate, relative to that in the fresh feed and 450.3 grams of distillate was recovered. After vacuum filtration, two water washes, and drying, 182.4 grams of a 74.8 wt % pure (anhydrous basis) KLG product was recovered corresponding to 63.1% KLG recovery. The composition of the resultant mother liquor is given in Table 2. Compared to Example 43, the increased concentration led to a greater surplus of protons as reflected by the ratio of available protons to KLG (202.5% versus 134.8%). There was also evidence for KLG decomposition as the ascorbic acid level in the mother liquor was 1.57 wt %.

In all of these cases (Examples 1–44), no attempt was made to adjust the protonation level of the pretreated broth based on charge balance calculations or titrations. As a result, the crystallization feeds were either under- or overacidified leading to high KLG solubilities or KLG decomposition, respectively, upon concentration by evaporation. In the following examples, KLG protonation was adjusted in a final base or acid addition step before crystallization such that the molar ratio of available protons to KLG was targeted to be one (i.e., equivalence).

Example 45

The same broth used as the fresh feed in Examples 23–25 was further pretreated by contact with the hydrogen form of a cation exchange resin much like the fresh feed used in Examples 14–16. Three separate batches were prepared (designated 45A, 45B, and 45C) with compositions given in Table 3. Based on charge balance calculations, sodium hydroxide (2.4 grams/kg broth) was added to the blended broth to bring the ratio of available protons to KLG near 100%. The resultant broth had a composition given in Table 1, of which 9000 grams was subjected to evaporative crystallization at 10° C. The broth was evaporated to the point at which the average concentration of soluble inorganics (Na and P) increased by a factor of 6.69 in the mother liquor, or filtrate, relative to that in the feed and 6869.2 grams of distillate was recovered. After vacuum filtration, two water washes, and drying, 700.4 grams of a 84.1 wt % pure (anhydrous basis) KLG product was recovered corresponding to 63.2% KLG recovery. The composition of the mother liquor is given in Table 2. Sodium hydroxide addition was very effective in reducing the overprotonation resulting from cation exchange as the ratio of available protons to KLG in the feed was 101.9% and increased to only 105.7% in the mother liquor.

Example 46

To simulate mother liquor recycle in a continuous crystallization process, 1109.8 grams of the mother liquor from the batch crystallization described in Example 45 was subjected to further evaporative crystallization at 10° C. The broth was evaporated to the point at which the average concentration of soluble inorganics (Na and P) increased by a factor of 14.77 in the mother liquor, or filtrate, relative to that in the fresh feed and 451.7 grams of distillate was recovered. After vacuum filtration, two water washes, and drying, 148.6 grams of a 82.9 wt % pure (anhydrous basis) KLG product was recovered corresponding to 51.7% KLG recovery. The composition of the resultant mother liquor is given in Table 2. Consistent with the increased concentration and KLG precipitation, there was a slightly greater surplus of protons as reflected by the ratio of available protons to KLG in the mother liquor (113.5% versus 105.7% in Example 45). However, this degree of over acidification was quite modest relative to that observed at similar concentration levels in Example 44 where sodium sulfate was added to the same cation exchanged broth instead of sodium hydroxide. The degree of KLG decomposition was reduced as ascorbic acid levels in the mother liquor were only 0.88 wt % in this case compared to 1.57 wt % in Example 44.

Example 47

As suggested by the nearly identical compositions in Table 1, 9000.4 grams of the same broth used as the fresh feed in Example 45 was again subjected to evaporative crystallization at 10° C. The broth was evaporated to the point at which the average concentration of soluble inorganics (Na and P) increased by a factor of 6.48 in the mother liquor, or filtrate, relative to that in the feed and 6902.4 grams of distillate was recovered. After vacuum filtration, two water washes, and drying, 708.5 grams of a 85.9 wt % pure (anhydrous basis) KLG product was recovered corresponding to 65.2% KLG recovery. The composition of the mother liquor is given in Table 2. Again, sodium hydroxide addition was very effective in reducing the overprotonation resulting from cation exchange as the ratio of available protons to KLG in the feed was 102.1% and increased to only 105.6% in the mother liquor.

Example 48

To simulate mother liquor recycle in a continuous crystallization process, 1117.8 grams of the mother liquor from the batch crystallization described in Example 47 was subjected to further evaporative crystallization at 10° C. The broth was evaporated to the point at which the average concentration of soluble inorganics (Na and P) increased by a factor of 15.24 in the mother liquor, or filtrate, relative to that in the fresh feed and 452.3 grams of distillate was recovered. After vacuum filtration, two water washes, and drying, 248.8 grams of a 70.4 wt % pure (anhydrous basis) KLG product was recovered corresponding to 70.9% KLG recovery. The composition of the resultant mother liquor is given in Table 2. Consistent with the increased concentration and KLG precipitation relative to Example 46, there was a slightly greater surplus of protons as reflected by the ratio of available protons to KLG in the mother liquor (117.7% versus 113.5%). Again, however, this degree of over acidification was quite modest relative to that observed in

27

Example 44 where sodium sulfate was added to the same cation exchanged broth instead of sodium hydroxide. The degree of KLG decomposition was again low, as the ascorbic acid level in the mother liquor was only 0.89 wt %.

Example 49

After acidification to pH~2 with sulfuric acid, carbon treatment, and microfiltration to remove cells, carbon, and other solids, a broth was further pretreated by contact with the hydrogen form of a cation exchange resin. Two separate batches were prepared (designated 49A and 49B) with compositions given in Table 3. A one-ml sample of each was transferred to a 100-ml titration vessel and mixed with 0.2 ml of a 1M barium chloride solution. (This amount of barium chloride was in excess relative to the sulfate present in the sample.) To each solution was added 75 ml of dimethyl sulfoxide (DMSO) and 0.3 ml of 0.5M sodium hydroxide. Each solution was then titrated to equivalence with a 0.1M solution of sodium triflic acid in DMSO. By titration, 0.0445 and 0.0326 moles of base per kg of broth were needed to bring solutions 49A and 49B, respectively, to equivalence.

Charge balance calculations were also performed for these broths. By charge balance, 0.0445 and 0.0324 moles of base per kg of broth were needed to bring solutions 49A and 49B, respectively, to equivalence thereby establishing either method as a valid means to measure the state of protonation.

After addition of 1.78 and 1.31 grams of NaOH per kg of broths 49A and 49B, respectively, to bring them to equivalence, the broths were blended together. The resultant broth had a composition given in Table 1, of which 6500.1 grams was subjected to evaporative crystallization at 10° C. The broth was evaporated to the point at which the average concentration of soluble inorganics (Na, Mg, and P) increased by a factor of 5.36 in the mother liquor, or filtrate, relative to that in the feed and 4596.7 grams of distillate was recovered. After vacuum filtration, two water washes, and drying, 695.5 grams of a 90.4 wt % pure (anhydrous basis) KLG product was recovered corresponding to 69.6% KLG recovery. The composition of the mother liquor is given in Table 2. Again, sodium hydroxide addition was very effective in reducing the overprotonation resulting from cation exchange as the ratio of available protons to KLG in the feed was 100.7% and increased to only 101.4% in the mother liquor. This was also reflected by the modest decrease in pH from 1.36 in the feed to 1.18 in the mother liquor.

Example 50

To simulate mother liquor recycle in a continuous crystallization process, 894.7 grams of the mother liquor from the batch crystallization described in Example 49 was subjected to further evaporative crystallization at 10° C. The broth was evaporated to the point at which the average concentration of soluble inorganics (Na, Mg, and P) increased by a factor of 16.07 in the mother liquor, or filtrate, relative to that in the fresh feed and 396.6 grams of distillate was recovered. After vacuum filtration, two water washes, and drying, 194.5 grams of a 77.0 wt % pure (anhydrous basis) KLG product was recovered corresponding to 62.5% KLG recovery. The composition of the resultant mother liquor is given in Table 2. Consistent with the increased concentration and KLG precipitation relative to Example 49, there was a slightly greater surplus of protons as reflected by the ratio of available protons to KLG in the mother liquor (105.3% versus 101.4%). Again, however, this degree of over acidification was quite modest as the pH of the second-stage mother liquor dropped to only 1.13.

28

Example 51

As suggested by the nearly identical compositions in Table 1, 6500.5 grams of the same broth used as the fresh feed in Example 49 was again subjected to evaporative crystallization at 10° C. The broth was evaporated to the point at which the average concentration of soluble inorganics (Na, Mg, and P) increased by a factor of 5.31 in the mother liquor, or filtrate, relative to that in the feed and 4612.1 grams of distillate was recovered. After vacuum filtration, two water washes, and drying, 683.7 grams of a 84.7 wt % pure (anhydrous basis) KLG product was recovered corresponding to 65.8% KLG recovery. The composition of the mother liquor is given in Table 2. Again, sodium hydroxide addition was very effective in reducing the overprotonation resulting from cation exchange as the ratio of available protons to KLG in the feed was 100.6% and increased to only 101.6% in the mother liquor. This was also reflected by the modest decrease in pH from 1.33 in the feed to 1.21 in the mother liquor.

Example 52

To simulate mother liquor recycle in a continuous crystallization process, 1045.9 grams of the mother liquor from the batch crystallization described in Example 51 was subjected to further evaporative crystallization at 10° C. The broth was evaporated to the point at which the average concentration of soluble inorganics (Na, Mg, and P) increased by a factor of 13.79 in the mother liquor, or filtrate, relative to that in the fresh feed and 439.6 grams of distillate was recovered. After vacuum filtration, two water washes, and drying, 192.6 grams of a 85.9 wt % pure (anhydrous basis) KLG product was recovered corresponding to 63.0% KLG recovery. The composition of the resultant mother liquor is given in Table 2. Consistent with the increased concentration and KLG precipitation relative to Example 51, there was a slightly greater surplus of protons as reflected by the ratio of available protons to KLG in the mother liquor (104.0% versus 101.6%). Again, however, this degree of over acidification was quite modest, as the pH of the second-stage mother liquor dropped to only 1.18 and ascorbic acid content was only 1.02 wt %.

Example 53

After acidification to pH~2 with sulfuric acid, carbon treatment, and microfiltration to remove cells, carbon, and other solids, a broth was further pretreated by contact with the hydrogen form of a cation exchange resin. A portion of this cation-exchanged broth was further pretreated by contact with the hydroxyl form of an anion exchange resin. To simulate a continuous crystallization process with cation exchange of the fresh feed and anion exchange of the recycled mother liquor, some of the cation-exchanged only broth was combined with the cation- and anion-exchanged broth and sodium hydroxide such that the combined feed was near equivalence. The resultant broth had a composition given in Table 1, of which 9002.4 grams was subjected to evaporative crystallization at 10° C. The broth was evaporated to the point at which the average concentration of soluble inorganics (Na, S, and P) increased by a factor of 7.65 in the mother liquor, or filtrate, relative to that in the feed and 7131.8 grams of distillate was recovered. After vacuum filtration, two water washes, and drying, 652.4 grams of a 87.0 wt % pure (anhydrous basis) KLG product was recovered corresponding to 67.5% KLG recovery. The composition of the mother liquor is given in Table 2. The combination of partial anion exchange and sodium hydroxide addition was effective in reducing the overprotonation resulting from cation exchange as the ratio of available protons to KLG in the feed was 102.0% and increased to only 106.7% in the mother liquor.

Example 54

To further simulate mother liquor recycle and increased recovery from increasing concentrations, 971.6 grams of the mother liquor from the batch crystallization described in Example 53 was subjected to further evaporative crystallization at 10° C. The broth was evaporated to the point at which the average concentration of soluble inorganics (Na, S, and P) increased by a factor of 19.92 in the mother liquor, or filtrate, relative to that in the fresh feed and 466.9 grams of distillate was recovered. After vacuum filtration, two water washes, and drying, 147.4 grams of a 81.8 wt % pure (anhydrous basis) KLG product was recovered corresponding to 53.5% KLG recovery. The composition of the resultant mother liquor is given in Table 2. Consistent with the increased concentration and KLG precipitation relative to Example 53, there was a greater surplus of protons as reflected by the ratio of available protons to KLG in the mother liquor (119.7% versus 106.7%). Even at nearly 20-fold concentration, this degree of over acidification was modest, as the pH of the second-stage mother liquor dropped to only 0.63 and ascorbic acid content was only 1.51 wt %.

Example 55

As suggested by the nearly identical compositions in Table 1, 9000.1 grams of the same broth used as the fresh feed in Example 53 was again subjected to evaporative crystallization at 10° C. The broth was evaporated to the point at which the average concentration of soluble inorganics (Na, S, and P) increased by a factor of 7.30 in the mother liquor, or filtrate, relative to that in the feed and 7118.2 grams of distillate was recovered. After vacuum filtration, two water washes, and drying, 647.6 grams of a 89.2 wt % pure (anhydrous basis) KLG product was recovered corresponding to 69.1% KLG recovery. The composition of the mother liquor is given in Table 2. Again, the combination of partial anion exchange and sodium hydroxide addition was effective in reducing the overprotonation resulting from cation exchange as the ratio of available protons to KLG in the feed was 102.1% and increased to only 105.9% in the mother liquor.

Example 56

To further simulate mother liquor recycle and increased recovery from increasing concentrations, 997.3 grams of the mother liquor from the batch crystallization described in Example 55 was subjected to further evaporative crystallization at 10° C. The broth was evaporated to the point at which the average concentration of soluble inorganics (Na, S, and P) increased by a factor of 16.85 in the mother liquor, or filtrate, relative to that in the fresh feed and 514.8 grams of distillate was recovered. After vacuum filtration, two water washes, and drying, 156.4 grams of a 84.5 wt % pure (anhydrous basis) KLG product was recovered corresponding to 57.3% KLG recovery. The composition of the resultant mother liquor is given in Table 2. Consistent with the increased concentration and KLG precipitation relative to Example 55, there was a greater surplus of protons as reflected by the ratio of available protons to KLG in the mother liquor (115.2% versus 105.9%). The slightly higher pH of the second-stage mother liquor (0.66 versus 0.63) and lower ascorbic acid level (1.27 versus 1.51 wt %) relative to Example 54 likely reflect the smaller degree of concentration.

Example 57

After microfiltration at pH~5.5 to remove cells, acidification to pH~2.3 with sulfuric acid, carbon treatment, and filtration to remove carbon and other solids, a broth was further pretreated by adding more sulfuric acid (to pH 1.8), filtration, and contact with the hydrogen form of a cation exchange resin. Based on charge balance calculations using the pretreated broth composition in Table 3, sodium hydroxide (2.94 grams/kg broth) was added to the blended broth to bring it near equivalence. The resultant broth had a composition given in Table 1, of which 9000 grams was subjected to evaporative crystallization at 10° C. The broth was evaporated to the point at which the average concentration of soluble inorganics (K, Na, Mg, Cl, and P) increased by a factor of 7.63 in the mother liquor, or filtrate, relative to that in the feed and 6972.9 grams of distillate was recovered. After vacuum filtration, two water washes, and drying, 869.3 grams of a 87.9 wt % pure (anhydrous basis) KLG product was recovered corresponding to 76.5% KLG recovery. The composition of the mother liquor is given in Table 2. Sodium hydroxide addition was very effective in reducing the overprotonation resulting from cation exchange as the ratio of available protons to KLG in the feed was 99.6% and increased to only 100.8% in the mother liquor. This was also reflected by the small decrease in pH from 1.52 to 1.25 and the low level of ascorbic acid generated (0.34 wt %).

Example 58

As suggested by the nearly identical compositions in Table 1, 9000.4 grams of the same broth used as the fresh feed in Example 57 was again subjected to evaporative crystallization at 10° C. The broth was evaporated to the point at which the average concentration of soluble inorganics (K, Na, Mg, Cl, and P) increased by a factor of 7.37 in the mother liquor, or filtrate, relative to that in the feed and 6955.5 grams of distillate was recovered. After vacuum filtration, two water washes, and drying, 838.6 grams of a 82.7 wt % pure (anhydrous basis) KLG product was recovered corresponding to 64.6% KLG recovery. The composition of the mother liquor is given in Table 2. Again, sodium hydroxide addition was very effective in reducing the overprotonation resulting from cation exchange as the ratio of available protons to KLG in the feed was 100.6% and increased to only 101.6% in the mother liquor. This was also reflected by the small decrease in pH from 1.52 in the feed to 1.3 in the mother liquor and the low ascorbic acid level of 0.37 wt %.

Example 59

After microfiltration at pH~5.5 to remove cells, acidification to pH~2.3 with sulfuric acid, carbon treatment, and filtration to remove carbon and other solids, a broth was further pretreated by adding more sulfuric acid (to pH 1.8), filtration, and contact with the hydrogen form of a cation exchange resin. A portion of this cation-exchanged broth was further pretreated by contact with the hydroxyl form of an anion exchange resin. To simulate a continuous crystallization process with cation exchange of the fresh feed and anion exchange of the recycled mother liquor, some of the cation-exchanged only broth was combined with the cation- and anion-exchanged broth and both sodium hydroxide and sulfuric acid such that the combined feed was near equivalence. The resultant broth had a composition given in Table 1, of which 9000.4 grams was subjected to evaporative crystallization at 10° C. The broth was evaporated to the point at which the average concentration of soluble inorganics (K, Na, Mg, Cl, and P) increased by a factor of 6.96 in the mother liquor, or filtrate, relative to that in the feed and 7001 grams of distillate was recovered. After vacuum filtration, two water washes, and drying, 720.2 grams of a 86.3 wt % pure (anhydrous basis) KLG product was recovered corresponding to 64.0% KLG recovery. The composition of the mother liquor is given in Table 2. The combination of partial anion exchange and sodium hydroxide addition was effective in reducing the overprotonation resulting from cation exchange as the ratio of available protons to KLG in the feed was 100.8% and increased to only 103.0% in the mother liquor. This was also reflected by the small decrease in pH from 1.51 in the feed to 1.34 in the mother liquor and the low ascorbic acid level of 0.40 wt %.

Example 60

As suggested by the nearly identical compositions in Table 1, 9000.1 grams of the same broth used as the fresh feed in Example 59 was again subjected to evaporative crystallization at 10° C. The broth was evaporated to the point at which the average concentration of soluble inorganics (K, Na, Mg, Cl, and P) increased by a factor of 7.05 in the mother liquor, or filtrate, relative to that in the feed and 7001.2 grams of distillate was recovered. After vacuum filtration, two water washes, and drying, 700.8 grams of a 87.1 wt % pure (anhydrous basis) KLG product was recovered corresponding to 67.6% KLG recovery. The composition of the mother liquor is given in Table 2. Again, the combination of partial anion exchange and sodium hydroxide addition was effective in reducing the overprotonation resulting from cation exchange as the ratio of available protons to KLG in the feed was 101.0% and increased to only 102.9% in the mother liquor. And, KLG decomposition was minimal as indicated by the low ascorbic acid level of 0.44 wt % in the mother liquor.

Example 61

After microfiltration at pH~5.5 to remove cells, acidification to pH~2 with sulfuric acid, carbon treatment, and filtration to remove carbon and other solids, a broth was further pretreated by contact with the hydrogen form of a cation exchange resin. A portion of this cation-exchanged broth was further pretreated by contact with the hydroxyl form of an anion exchange resin. To simulate a continuous crystallization process with cation exchange of the fresh feed and anion exchange of the recycled mother liquor, some of the cation-exchanged only broth was combined with the cation- and anion-exchanged broth such that the composite feed was near equivalence. The resultant broth had a composition given in Table 1, of which 9000.1 grams was subjected to evaporative crystallization at 10° C. The broth was evaporated to the point at which the average concentration of soluble inorganics (K, Na, Mg, and P) increased by a factor of 9.82 in the mother liquor, or filtrate, relative to that in the feed and 7412.7 grams of distillate was recovered. After vacuum filtration, two water washes, and drying, 671.1 grams of a 85.5 wt % pure (anhydrous basis) KLG product was recovered corresponding to 70.3% KLG recovery. The composition of the mother liquor is given in Table 2. Because the cation exchange was relatively incomplete, the feed was somewhat underprotonated as reflected by the ratio of available protons to KLG of 97.7% and becomes lightly more so (93.5%) in the resulting mother liquor.

Example 62

As suggested by the nearly identical compositions in Table 1, 9000.7 grams of the same broth used as the fresh feed in Example 61 was again subjected to evaporative crystallization at 10° C. The broth was evaporated to the point at which the average concentration of soluble inorganics (K, Na, Mg, Cl, and P) increased by a factor of 9.26 in the mother liquor, or filtrate, relative to that in the feed and 7366.2 grams of distillate was recovered. After vacuum filtration, two water washes, and drying, 630.1 grams of a 87.9 wt % pure (anhydrous basis) KLG product was recovered corresponding to 74.9% KLG recovery. The composition of the mother liquor is given in Table 2. Again, because the cation exchange was relatively incomplete, the feed was somewhat underprotonated as reflected by the ratio of available protons to KLG of 97.4% and becomes lightly more so (93.5%) in the resulting mother liquor. KLG decomposition was minimal as indicated by the low ascorbic acid level of 0.37 wt % in the mother liquor.

Example 63

After microfiltration at pH~5.5 to remove cells, acidification to pH~2 with sulfuric acid, and filtration to remove solids, a broth was further pretreated by contact with the hydrogen form of a cation exchange resin. Based on charge balance calculations using the pretreated broth composition in Table 3, sodium hydroxide (7.5 grams/kg broth) was added to the blended broth to bring it near equivalence. The resultant broth had a composition given in Table 1, of which 8999.5 grams was subjected to evaporative crystallization at 10° C. The broth was evaporated to the point at which the average concentration of soluble inorganics (Na, Mg, Cl, and P) increased by a factor of 7.12 in the mother liquor, or filtrate, relative to that in the feed and 6541.2 grams of distillate was recovered. After vacuum filtration, two water washes, and drying, 975.7 grams of a 80.6 wt % pure (anhydrous basis) KLG product was recovered corresponding to 72.3% KLG recovery. The composition of the mother liquor is given in Table 2. Sodium hydroxide addition was effective in reducing the overprotonation resulting from cation exchange as the ratio of available protons to KLG in the feed was 102.3% and increased to only 106.2% in the mother liquor. KLG decomposition was minimal as indicated by the low ascorbic acid level of 0.60 wt % in the mother liquor.

Example 64

To simulate mother liquor recycle in a continuous crystallization process, 921.5 grams of the mother liquor from the batch crystallization described in Example 63 was subjected to further evaporative crystallization at 10° C. The broth was evaporated to the point at which the average concentration of soluble inorganics (Na, Mg, Cl, and P) increased by a factor of 8.74 in the mother liquor, or filtrate, relative to that in the fresh feed and 232.2 grams of distillate was recovered. After vacuum filtration, two water washes, and drying, 73.3 grams of a 76.0 wt % pure (anhydrous basis) KLG product was recovered corresponding to 27.5% KLG recovery. The composition of the resultant mother liquor is given in Table 2. Consistent with the increased concentration and KLG precipitation relative to Example 63, there was a greater surplus of protons as reflected by the ratio of available protons to KLG in the mother liquor (116.0% versus 106.2%). Again, however, this degree of over acidification was quite modest, as the ascorbic acid content of the second-stage mother liquor was only 0.94 wt %.

Example 65

After microfiltration at pH~5.5 to remove cells, acidification to pH~2 with sulfuric acid, carbon treatment, and filtration to remove carbon and other solids, a broth was further pretreated by contact with the hydrogen form of a cation exchange resin. A portion of this cation-exchanged broth was further pretreated by contact with the hydroxyl form of an anion exchange resin. To simulate a continuous crystallization process with cation exchange of the fresh feed and anion exchange of the recycled mother liquor, some of the cation-exchanged only broth was combined with the cation- and anion-exchanged broth and sodium hydroxide such that the composite feed was near equivalence. The resultant broth had a composition given in Table 1, of which 9000.1 grams was subjected to evaporative crystallization at 10 °C. The broth was evaporated to the point at which the average concentration of soluble inorganics (S, Cl, and P) increased by a factor of 6.05 in the mother liquor, or filtrate, relative to that in the feed and 6717.2 grams of distillate was recovered. After vacuum filtration, two water washes, and drying, 655 grams of a 85.7 wt % pure (anhydrous basis) KLG product was recovered corresponding to 55.4% KLG recovery. The composition of the mother liquor is given in Table 2. The combination of partial anion exchange and sodium hydroxide addition was effective in reducing the overprotonation resulting from cation exchange as the ratio of available protons to KLG in the feed was 100.4% and increased to only 101.7% in the mother liquor. KLG decomposition was also low as reflected by the ascorbic acid level of 0.41 wt % in the mother liquor.

Example 66

To further simulate mother liquor recycle and increased recovery from increasing concentrations, 934.2 grams of the mother liquor from the batch crystallization described in Example 65 was subjected to further evaporative crystallization at 10° C. The broth was evaporated to the point at which the average concentration of soluble inorganics (S, Cl, and P) increased by a factor of 27.02 in the mother liquor, or filtrate, relative to that in the fresh feed and 476.8 grams of distillate was recovered. After vacuum filtration, two water washes, and drying, 194.2 grams of a 79.3 wt % pure (anhydrous basis) KLG product was recovered corresponding to 66.7% KLG recovery. The composition of the resultant mother liquor is given in Table 2. Even at nearly 30-fold concentration, the mother liquor remained near equivalence as the ratio of available protons to KLG increased to only 108.1%.

Example 67

After microfiltration at pH~5.5 to remove cells, acidification to pH~2 with sulfuric acid, and filtration to remove solids, a broth was further pretreated by contact with the hydrogen form of a cation exchange resin. A portion of this cation-exchanged broth was further pretreated by contact with the hydroxyl form of an anion exchange resin. To simulate a continuous crystallization process with cation exchange of the fresh feed and anion exchange of the recycled mother liquor, some of the cation-exchanged only broth was combined with the cation- and anion-exchanged broth and sodium hydroxide such that the composite feed was near equivalence. The resultant broth had a composition given in Table 1, of which 9000.2 grams was subjected to evaporative crystallization at 10° C. The broth was evaporated to the point at which the average concentration of soluble inorganics (Na, S, Cl, and P) increased by a factor of 6.87 in the mother liquor, or filtrate, relative to that in the feed and 6925 grams of distillate was recovered. After vacuum filtration, two water washes, and drying, 689.7 grams of a 85.6 wt % pure (anhydrous basis) KBLG product was recovered corresponding to 58.9% KBLG recovery. The composition of the mother liquor is given in Table 2. Again, the combination of partial anion exchange and sodium hydroxide addition was effective in reducing the overprotonation resulting from cation exchange as the ratio of available protons to KLG in the feed was 100.3% and increased to only 101.8% in the mother liquor.

Example 68

To further simulate mother liquor recycle and increased recovery from increasing concentrations, 1054.9 grams of the mother liquor from the batch crystallization described in Example 67 was subjected to further evaporative crystallization at 10° C. The broth was evaporated to the point at which the average concentration of soluble inorganics (Na, S, Cl, and P) increased by a factor of 16.33 in the mother liquor, or filtrate, relative to that in the fresh feed and 522.3 grams of distillate was recovered. After vacuum filtration, two water washes, and drying, 177.3 grams of a 74.3 wt % pure (anhydrous basis) KLG product was recovered corresponding to 51.1% KLG recovery. The composition of the resultant mother liquor is given in Table 2. Again, the combination of partial anion exchange and sodium hydroxide addition was effective in reducing the overprotonation resulting from cation exchange as the ratio of available protons to KLG increased to only 106.2% in the second-stage mother liquor.

Example 69

After microfiltration at pH~5.5 to remove cells, acidification to pH~2 with sulfuric acid, carbon treatment, and microfiltration to remove cells, carbon and other solids, a broth was further pretreated by adding more sulfuric acid and filtration. Based on charge balance calculations using the pretreated broth composition in Table 3, the additional sulfuric acid (5.31 grams/kg of broth) was that required to bring the solution near equivalence. The resultant broth had a composition given in Table 1, of which 9000 grams was subjected to evaporative crystallization at 10° C. The broth was evaporated to the point at which the average concentration of soluble inorganics (K, Na, Mg, Cl, and P) increased by a factor of 4.89 in the mother liquor, or filtrate, relative to that in the feed and 6236.4 grams of distillate was recovered. After vacuum filtration, two water washes, and drying, 861.6 grams of a 83.5 wt % pure (anhydrous basis) KLG product was recovered corresponding to 60.0% KLG recovery. The composition of the mother liquor is given in Table 2. Apparently the amount of sulfuric acid added was insufficient to reach equivalence as the feed was somewhat underprotonated as reflected by the ratio of available protons to KLG of 97.0%, and becomes lightly more so (94.0%) in the resulting mother liquor.

Example 70

To simulate mother liquor recycle in a continuous crystallization process, 1434.4 grams of the mother liquor from the batch crystallization described in Example 69 was subjected to further evaporative crystallization at 10° C. The broth was evaporated to the point at which the average concentration of soluble inorganics (K, Na, Mg, Cl, and P) increased by a factor of 11.63 in the mother liquor, or filtrate, relative to that in the fresh feed and 664.6 grams of distillate was recovered. After vacuum filtration, two water washes, and drying, 257.4 grams of a 82.1 wt % pure (anhydrous basis) KLG product was recovered corresponding to 56.4% KLG recovery. The composition of the resultant mother liquor is given in Table 2. Consistent with the increased concentration and KLG precipitation relative to Example 63, there was a greater deficit of protons as reflected by the ratio of available protons to KLG in the mother liquor (88.24% versus 94.0%). Again, however, this degree of under acidification was quite modest. And the ascorbic acid content of the second-stage mother liquor of only 0.82 wt % demonstrates that ion exchange is not necessary to avoid KLG decomposition.

TABLE 1

Compositional Analyses and Charge Balance Calculations for Crystalization Feeds

| Example | KLG wt % | Ca | K | Na | Mg | P | S | Cl* | Implied, ppm H₃O⁺ | OH⁻ | Protons/KLG, % Total | Avail. |
|---|---|---|---|---|---|---|---|---|---|---|---|---|
| 1 | 13.25 | 1660 | 1670 | 880 | 0 | 540 | 880 | 221.4 | 0 | 857 | 92.6 | 87.5 |
| 3 | 12.00 | 0 | 0 | 0 | 0 | 510 | 835 | 209.1 | 2043 | 0 | 117.4 | 112.1 |
| 6 | 8.90 | 2.8 | 0 | 11.7 | 0.58 | 174 | 2482 | 287.1 | 3407 | 0 | 139.1 | 136.6 |
| 8 | 10.89 | 0 | 0 | 7 | 0 | 123 | 3789 | 203.0 | 4827 | 0 | 145.2 | 143.8 |
| 11 | 12.27 | 0 | 0 | 7.83 | 0 | 488.5 | 3849 | 200.3 | 5569 | 0 | 146.3 | 141.3 |
| 14 | 8.31 | 0 | 0 | 10.6 | 0 | 92.5 | 762.3 | 152.6 | 1148 | 0 | 114.1 | 112.7 |
| 17 | 13.23 | 637 | 1700 | 822 | 157 | 508 | 2796 | 208.3 | 2009 | 0 | 115.5 | 110.7 |
| 20 | 12.35 | 695 | 1100 | 778 | 151 | 126 | 2605 | 207.9 | 1361 | 0 | 111.3 | 110.0 |
| 23 | 12.12 | 1050 | 1580 | 832 | 152 | 131 | 1035 | 216.2 | 0 | 989 | 90.7 | 89.3 |
| 26 | 12.28 | 18 | 56 | 200 | 4 | 126 | 3400 | 207.9 | 4163 | 0 | 134.6 | 133.3 |
| 29 | 11.14 | 15 | 143 | 372 | 6 | 508 | 806 | 208.3 | 1603 | 0 | 114.7 | 109.0 |
| 32 | 11.46 | 5 | 0 | 99.8 | 0.8 | 129 | 3100 | 212.9 | 3943 | 0 | 135.1 | 133.7 |
| 35 | 8.30 | 41 | 173 | 288.1 | 31.7 | 9 | 1.8 | 30 | 0 | 336 | 95.4 | 95.2 |
| 37 | 8.38 | 41 | 168 | 292 | 31.3 | 6 | 8.2 | 26 | 0 | 337 | 95.4 | 95.3 |
| 39 | 12.07 | 885 | 1700 | 900.8 | 158 | 529 | 3000 | 218 | 1993 | 0 | 116.9 | 111.4 |
| 41 | 12.03 | 529 | 1700 | 912 | 160 | 536 | 2600 | 233 | 1864 | 0 | 115.8 | 110.2 |
| 43 | 10.29 | 2 | 32 | 1400 | 0.7 | 121 | 1700 | 199.7 | 1171 | 0 | 111.6 | 110.1 |
| 45 | 10.36 | 3 | 32 | 1400 | 0.9 | 122 | 1000 | 201.3 | 342 | 0 | 103.4 | 101.9 |
| 47 | 10.37 | 5 | 36 | 1400 | 0.9 | 125 | 1000 | 252 | 370 | 0 | 103.7 | 102.1 |
| 49 | 13.89 | 101 | 53 | 1000 | 9.9 | 180 | 645.8 | 345.6 | 319 | 0 | 102.3 | 100.7 |
| 51 | 13.55 | 102 | 58 | 1000 | 9.9 | 177 | 637 | 334 | 293 | 0 | 102.2 | 100.6 |
| 53 | 9.34 | 0 | 0 | 248.1 | 0 | 140 | 230 | 57.4 | 356 | 0 | 103.9 | 102.0 |
| 55 | 9.29 | 0 | 0 | 248 | 0.9 | 142 | 224 | 78 | 363 | 0 | 104.0 | 102.1 |
| 57 | 11.09 | 253 | 177 | 2000 | 26.5 | 241 | 1400 | 317 | 253 | 0 | 102.3 | 99.6 |
| 58 | 11.93 | 257 | 178 | 2000 | 26.9 | 245 | 1500 | 309 | 370 | 0 | 103.2 | 100.6 |
| 59 | 10.79 | 158 | 160 | 644.3 | 22.7 | 84 | 654 | 89 | 182 | 0 | 101.7 | 100.8 |
| 60 | 10.03 | 161 | 177 | 655.3 | 23.2 | 85 | 686.1 | 87 | 200 | 0 | 102.0 | 101.0 |
| 61 | 9.07 | 129 | 219 | 426.5 | 28.8 | 81 | 270.1 | 97 | 0 | 94 | 98.8 | 97.7 |
| 62 | 8.21 | 131 | 216 | 428.4 | 29 | 81 | 270.1 | 90 | 0 | 99 | 98.6 | 97.4 |
| 63 | 12.09 | 0 | 0 | 4200 | 0.5 | 189 | 2900 | 363 | 509 | 0 | 104.3 | 102.3 |
| 65 | 11.25 | 7 | 7 | 168.6 | 0.6 | 13 | 134.4 | 55 | 62 | 0 | 100.6 | 100.4 |
| 67 | 11.14 | 1 | 0 | 420 | 0.2 | 107 | 220 | 111 | 169 | 0 | 101.6 | 100.3 |
| 69 | 13.33 | 905 | 934 | 641 | 137 | 176 | 1200 | 254 | 0 | 155 | 98.7 | 97.0 |

*Italicized chlorine levels were estimated from P/Cl ratios.

TABLE 2

Compositional Analyses and Charge Balance Calculations for Crystallization Mother Liquors

| Example | KLG wt % | AsA wt % | Ca | K | Na | Mg | P | S | Cl* | Protons/KLG, % Total | Avail. |
|---|---|---|---|---|---|---|---|---|---|---|---|
| 1 | 35.72 | 0 | 5600 | 11900 | 6900 | 1222 | 4100 | 1355 | 1681 | 75.2 | 60.9 |
| 2 | 19.96 | 0 | 4600 | 9700 | 5504 | 962 | 3200 | 1196 | 1312 | 63.6 | 43.5 |
| 3 | 21.72 | 1.39 | 60 | 6 | 24 | 0.6 | 2500 | 4121 | 1025 | 146.8 | 132.4 |
| 4 | 15.97 | 2.28 | 52 | 17 | 28 | 0.7 | 4400 | 7318 | 1804 | 213.0 | 178.4 |
| 5 | 16.47 | 2.81 | 43 | 12 | 35 | 0.7 | 6000 | 9874 | 2460 | 248.8 | 203.2 |
| 6 | 16.19 | 2.85 | 2 | 0 | 21 | 0.6 | 1100 | 20200 | 1815 | 269.9 | 261.4 |
| 7 | 14.81 | 3.14 | 0 | 0 | 12.8 | 0.5 | 2597 | 21200 | 4285 | 322.2 | 300.2 |
| 8 | 13.16 | 2 | 2 | 0 | 26.9 | 0.75 | 758 | 24000 | 1300 | 337.0 | 329.8 |
| 9 | 9.75 | 3.37 | 3 | 17 | 26 | 1 | 1261 | 39000 | 2100 | 620.4 | 604.2 |
| 10 | 10.6 | 3.21 | 2 | 8 | 25 | 0.51 | 1101 | 34000 | 1600 | 516.1 | 503.1 |
| 11 | 18.02 | 1.35 | 0 | 0 | 31 | 0.96 | 1964 | 15800 | 863 | 229.2 | 215.5 |
| 12 | 16.04 | 2.12 | 0 | 0 | 52 | 1.2 | 2880 | 23000 | 1200 | 311.3 | 288.8 |
| 13 | 12.19 | 4.87 | 0 | 0 | 68 | 1.7 | 5818 | 47000 | 2200 | 666.2 | 606.4 |
| 14 | 26.57 | 0.53 | 11 | 0 | 51 | 2 | 465 | 3809 | 767 | 122.0 | 119.8 |
| 15 | 22.25 | 0.93 | 0 | 0 | 11 | 0.6 | 650 | 5167 | 1073 | 136.2 | 132.6 |
| 16 | 20.22 | 1.67 | 0 | 0 | 13 | 0.58 | 839 | 6707 | 1500 | 152.0 | 146.8 |
| 17 | 21.36 | 0.44 | 209 | 14700 | 7209 | 1369 | 4531 | 20600 | 1900 | 187.7 | 161.1 |
| 18 | 22.63 | 0.028 | 181 | 13000 | 6902 | 1229 | 4200 | 18000 | 1722 | 171.7 | 148.4 |
| 19 | 21.78 | 0.34 | 124 | 17000 | 9495 | 1658 | 5600 | 25000 | 2296 | 204.9 | 172.7 |
| 20 | 21.36 | 0.28 | 205 | 12000 | 6615 | 1179 | 990 | 19000 | 1634 | 156.9 | 151.1 |
| 21 | 19.4 | 0.53 | 163 | 15900 | 8400 | 1500 | 1300 | 25100 | 2100 | 184.9 | 176.5 |
| 22 | 19.68 | 0.77 | 139 | 17000 | 9200 | 1600 | 1400 | 27000 | 2300 | 190.0 | 181.0 |
| 23 | 30.65 | 0.13 | 1500 | 11800 | 6600 | 1200 | 1000 | 3000 | 1700 | 72.7 | 68.6 |
| 24 | 32.87 | 0.22 | 1600 | 14700 | 8300 | 1500 | 1300 | 3400 | 2100 | 67.9 | 63.0 |
| 25 | 33.66 | 0.3 | 1600 | 15200 | 8700 | 1600 | 1400 | 3600 | 2600 | 68.6 | 63.3 |
| 26 | 17.01 | 0.86 | 123 | 342 | 1075 | 25 | 729 | 19700 | 1100 | 244.6 | 239.3 |
| 27 | 14.36 | 1.4 | 188 | 553 | 1806 | 41 | 1216 | 33000 | 2000 | 387.7 | 377.1 |

TABLE 2-continued

Compositional Analyses and Charge Balance Calculations for Crystallization Mother Liquors

| Example | KLG wt % | AsA wt % | Ca | K | Na | Ppm Mg | P | S | Cl* | Protons/KLG, % Total | Avail. |
|---|---|---|---|---|---|---|---|---|---|---|---|
| 28 | 14.73 | 2.02 | 195 | 596 | 2000 | 44.2 | 1300 | 36100 | 2145 | 406.3 | 395.2 |
| 29 | 22.35 | 0.59 | 103 | 808 | 2021 | 37 | 2986 | 4748 | 1200 | 143.7 | 126.9 |
| 30 | 18.39 | 1.22 | 167 | 1400 | 3600 | 66 | 5400 | 8600 | 2200 | 196.7 | 159.8 |
| 31 | 18.25 | 1.99 | 207 | 1900 | 4700 | 85.6 | 7000 | 11100 | 2800 | 225.4 | 177.4 |
| 32 | 16.07 | 0.76 | 27 | 126 | 607.4 | 6.2 | 750 | 18500 | 1200 | 248.5 | 242.7 |
| 33 | 12.22 | 1.4 | 52 | 226 | 1100 | 11.7 | 1400 | 34400 | 2100 | 462.9 | 448.6 |
| 34 | 13.66 | 2.65 | 60 | 262 | 1300 | 13.4 | 1600 | 40100 | 2400 | 477.7 | 463.0 |
| 35 | 25.18 | 0.11 | 163 | 690 | 1200 | 124.2 | 19 | 751.6 | 22 | 97.0 | 96.9 |
| 36 | 25.92 | 0.69 | 676 | 2800 | 4800 | 512.1 | 82 | 3200 | 19 | 88.9 | 88.5 |
| 37 | 23.83 | 0.11 | 161 | 686 | 1100 | 122.5 | 18 | 737.3 | 34 | 97.2 | 97.1 |
| 38 | 27.08 | 0.66 | 685 | 2800 | 4800 | 514.9 | 81 | 3200 | 50 | 89.4 | 89.0 |
| 39 | 23.16 | 0.74 | 210 | 8400 | 4600 | 800 | 2700 | 11800 | 1100 | 145.1 | 130.5 |
| 40 | 17.44 | 2.41 | 136 | 20100 | 11300 | 1900 | 6600 | 28400 | 2600 | 246.5 | 199.1 |
| 41 | 22.34 | 0.69 | 222 | 8100 | 4300 | 762.6 | 2600 | 10700 | 1100 | 141.9 | 127.3 |
| 42 | 17.99 | 1.82 | 126 | 20600 | 11300 | 2000 | 6700 | 28300 | 2600 | 240.2 | 193.5 |
| 43 | 19.48 | 0.61 | 22 | 228 | 8800 | 4.8 | 743 | 10900 | 1226 | 139.5 | 134.7 |
| 44 | 15.27 | 1.57 | 52 | 460 | 20200 | 11 | 1700 | 25100 | 2805 | 216.5 | 202.5 |
| 45 | 21.46 | 0.38 | 26 | 229 | 9300 | 5.1 | 821 | 6600 | 1300 | 110.5 | 105.7 |
| 46 | 20.79 | 0.88 | 90 | 492 | 20700 | 14.6 | 1800 | 14700 | 3100 | 124.3 | 113.5 |
| 47 | 22.09 | 0.43 | 24 | 225 | 9200 | 5.1 | 799 | 6500 | 1400 | 110.1 | 105.6 |
| 48 | 17.88 | 0.89 | 55 | 467 | 21400 | 12.2 | 1900 | 15400 | 3100 | 131.0 | 117.7 |
| 49 | 26.78 | 0.4 | 535 | 308 | 5500 | 51.9 | 960 | 3400 | 1900 | 105.8 | 101.4 |
| 50 | 24.68 | 1.27 | 200 | 882 | 16400 | 155.4 | 2900 | 9200 | 5600 | 120.0 | 105.3 |
| 51 | 25.12 | 0.34 | 525 | 310 | 5400 | 51.1 | 952 | 3400 | 1800 | 106.3 | 101.6 |
| 52 | 25.47 | 1.02 | 232 | 778 | 13900 | 132.1 | 2500 | 7800 | 4700 | 116.3 | 104.0 |
| 53 | 23.19 | 0 | 3 | 83 | 1800 | 0.1 | 1100 | 1800 | 445 | 112.6 | 106.7 |
| 54 | 18.10 | 1.51 | 9 | 262 | 4900 | 0.8 | 2800 | 4600 | 932 | 139.1 | 119.7 |
| 55 | 23.13 | 0.5 | 3 | 86 | 1800 | 0.4 | 1000 | 1700 | 428 | 111.3 | 105.9 |
| 56 | 19.98 | 1.27 | 7 | 216 | 4200 | 0.6 | 2300 | 3900 | 983 | 129.7 | 115.2 |
| 57 | 23.29 | 0.34 | 190 | 1300 | 15300 | 204 | 1900 | 9700 | 2400 | 111.0 | 100.8 |
| 58 | 23.11 | 0.37 | 193 | 1300 | 14800 | 198 | 1800 | 9600 | 2300 | 111.4 | 101.6 |
| 59 | 23.67 | 0.4 | 237 | 1100 | 4500 | 160.3 | 579 | 4000 | 623 | 106.1 | 103.0 |
| 60 | 25.11 | 0.44 | 242 | 1200 | 4600 | 163.2 | 598 | 4100 | 644 | 105.8 | 102.9 |
| 61 | 30.52 | 0 | 729 | 2100 | 4200 | 285.1 | 805 | 2300 | 861 | 96.8 | 93.5 |
| 62 | 28.25 | 0.37 | 738 | 2000 | 3900 | 270 | 764 | 2200 | 827 | 96.9 | 93.5 |
| 63 | 21.97 | 0.6 | 19 | 0 | 25000 | 5.6 | 1100 | 17100 | 2000 | 112.5 | 106.2 |
| 64 | 23.70 | 0.94 | 30 | 0 | 35600 | 4.2 | 1700 | 25600 | 3300 | 125.0 | 116.0 |
| 65 | 24.69 | 0.41 | 46 | 0 | 878 | 2.9 | 79 | 806 | 334 | 102.1 | 101.7 |
| 66 | 22.78 | 0 | 221 | 55 | 3900 | 12.9 | 351 | 3600 | 1500 | 110.0 | 108.1 |
| 67 | 24.46 | 0.92 | 8 | 0 | 2800 | 1 | 719 | 1600 | 755 | 105.4 | 101.8 |
| 68 | 15.61 | 1.62 | 20 | 0 | 6700 | 2.2 | 1700 | 3800 | 1800 | 119.9 | 106.2 |
| 69 | 26.12 | 0.02 | 615 | 4400 | 3100 | 665 | 874 | 3000 | 1300 | 98.2 | 94.0 |
| 70 | 27.82 | 0.82 | 622 | 10400 | 7200 | 1600 | 2100 | 6700 | 3100 | 97.7 | 88.2 |

*Italicized chlorine levels were estimated from P/Cl ratios.

TABLE 3

Compositional Analyses and Charge Balance Calculations for Pretreated Feeds Before Final Protonation Step

| Example | KLG wt % | Ca | K | ppm Na | Mg | P | S | Cl* | Implied, ppm $H_3O^+$ | $OH^-$ | Protons/KLG, % Total | Avail. |
|---|---|---|---|---|---|---|---|---|---|---|---|---|
| 45A | 11.05 | 4 | 24 | 105.6 | 1.1 | 118 | 890.2 | 194.7 | 1274 | 0 | 111.77 | 110.4 |
| 45B | 10.59 | 4 | 40 | 90.3 | 0.6 | 117 | 884.4 | 193.1 | 1270 | 0 | 112.24 | 110.9 |
| 45C | 10.44 | 3 | 39 | 80 | 0.4 | 114 | 865.1 | 188.1 | 1249 | 0 | 112.21 | 110.8 |
| 49A | 15.07 | 42 | 36 | 63 | 4.7 | 181 | 576 | 314.0 | 1069 | 0 | 107.2 | 105.7 |
| 49B | 15.47 | 157 | 75 | 172.5 | 14.8 | 184 | 576 | 319.2 | 842 | 0 | 105.6 | 104.1 |
| 57 | 11.07 | 263 | 184 | 390 | 27.6 | 249 | 1500 | 316 | 1704 | 0 | 115.7 | 112.9 |
| 63 | 12.49 | 0 | 0 | 47.9 | 0.5 | 189 | 2800 | 373 | 3831 | 0 | 131.3 | 129.4 |
| 69 | 14.05 | 2000 | 766 | 572 | 116 | 150 | 539 | 253 | 0 | 1676 | 86.4 | 85.0 |

*Italicized chlorine levels were estimated from P/Cl ratios.

While the present invention has been described in terms of certain embodiments thereof, it will recognized that various substitutions, modifications, alterations, omissions and other changes may be made without departing from the spirit thereof. Accordingly, the scope of the present invention is to amend only by the scope of the following claims, including equivalents thereof.

What is claimed is:

1. A method for recovering a degradation-sensitive organic acid or salt thereof comprising the steps of:
   (a) providing an aqueous composition comprising:
      (i) a degradation-sensitive organic acid selected from the group consisting of ascorbic acid, succinic acid, tartaric acid, glyconic acid, gluconic acid, gulonic acid, citric acid, lactic acid, malic acid, maleic acid, acetic acid, formic acid, pyruvic acid, propionic acid, butyric acid, itaconic acid, and mixtures thereof; and
      (ii) a solvent;
   (b) calculating a concentration of available protons in the aqueous composition;
   (c) calculating an amount of adjustment in the concentration of available protons necessary for equivalence of the organic acid;
   (d) adjusting the proton concentration of the organic acid to from about 90 to about 100% of equivalence; and
   (e) recovering the organic acid from the aqueous composition.

2. The method of claim 1 wherein the aqueous composition comprises anions, non-proton cations, protons, and weak acid anions; and wherein step (b) comprises the steps of:
   (a) determining a total concentration of anions;
   (b) determining a total concentration of non-proton cations;
   (c) calculating a total concentration of protons by subtracting the total concentration of anions from the total concentration of non-proton cations;
   (d) determining a total concentration of weak acid anions; and
   (e) calculating the concentration of available protons by subtracting the total concentration of weak acid anions from the total concentration of protons.

3. The method of claim 1 wherein the amount of adjustment necessary for equivalence is calculated from the concentration of available protons.

4. The method of claim 1 wherein the organic acid is 2-keto-L-galonic acid or 2-keto-D-gluconic acid.

5. The method of claim 1 wherein the providing step comprises producing the 2-keto-L-gulonic acid or 2-keto-D-gluconi acid by a fermentation reaction.

6. The method of claim 4 further comprising the step of converting the 2-keto-L-gulonic acid or 2-keto-D-gluconic acid to ascorbic acid or erythorbic acid.

7. The method of claim 1 wherein step (b) is conducted by determining the charge balance of the aqueous composition, by titration, or by spectroscopic methods.

8. The method of claim 1 wherein the adjusting step is conducted by addition of hydrochloric acid, sulfuric acid, nitric aid, or phosphoric acid to the aqueous composition.

9. The method of claim 1 wherein the adjusting step is conducted by addition of sodium hydroxide or potassium hydroxide to the aqueous composition.

10. The method of claim 1 wherein the adjusting step is conduct by addition of a salt form of the organic acid.

11. The method of claim 1 further comprising the step of recycling a stream recovered from step (e) by adding the stream to the process at a point before or during step (b).

12. The method of claim 1 wherein the recovering step comprises
   (i) crystallizing the organic acid from the solution and (ii) separating the crystallized organic acid from the aqueous composition by at least one of filtration, decantation, centrifugation, extraction, or spray drying.

* * * * *